(12) United States Patent
Sankaran et al.

(10) Patent No.: US 9,970,899 B2
(45) Date of Patent: May 15, 2018

(54) AUTOMATED SMART WATER QUALITY MONITOR AND ANALYZER AND ASSOCIATED METHODS

(71) Applicant: KETOS, INC., San Jose, CA (US)

(72) Inventors: Meena Sankaran, San Jose, CA (US); Mazhar N. Ali, Halle (DE); Harish Mehta, Lyndhurst, NJ (US)

(73) Assignee: KETOS, INC., San Jose, CA (US)

( * ) Notice: Subject to any disclaimer, the term of this patent is extended or adjusted under 35 U.S.C. 154(b) by 0 days. days.

(21) Appl. No.: 15/649,379

(22) Filed: Jul. 13, 2017

(65) Prior Publication Data

US 2018/0017526 A1   Jan. 18, 2018

Related U.S. Application Data

(60) Provisional application No. 62/363,135, filed on Jul. 15, 2016.

(51) Int. Cl.
| | |
|---|---|
| *G01N 27/403* | (2006.01) |
| *G01N 27/48* | (2006.01) |
| *G01N 15/06* | (2006.01) |
| *G01N 27/333* | (2006.01) |
| *G01N 15/00* | (2006.01) |
| *G01N 33/18* | (2006.01) |
| *G01N 27/416* | (2006.01) |

(52) U.S. Cl.
CPC ......... *G01N 27/48* (2013.01); *G01N 15/0656* (2013.01); *G01N 27/333* (2013.01); *G01N 27/403* (2013.01); *G01N 27/416* (2013.01); *G01N 33/18* (2013.01); *G01N 2015/0053* (2013.01)

(58) Field of Classification Search
CPC ... G01N 27/333; G01N 27/403; G01N 27/416
See application file for complete search history.

(56) References Cited

U.S. PATENT DOCUMENTS

| | | | |
|---|---|---|---|
| 3,904,487 A | 9/1975 | Lieberman et al. | |
| 3,997,420 A * | 12/1976 | Buzza | G01N 33/4925 204/411 |
| 4,019,861 A * | 4/1977 | Dahms | G01N 31/00 204/405 |

(Continued)

FOREIGN PATENT DOCUMENTS

| | | |
|---|---|---|
| CN | 102445488 A | 5/2012 |
| CN | 102830237 A | 12/2012 |

(Continued)

OTHER PUBLICATIONS

International Search Report for PCT Application PCT/US2017/041985, dated Nov. 6, 2017, in 21 pages.

*Primary Examiner* — Alexander S Noguerola
(74) *Attorney, Agent, or Firm* — Knobbe Martens Olson & Bear LLP

(57) ABSTRACT

A fluid testing system can be used to measure the levels of contaminants in a fluid system. The system can utilize anodic stripping voltammetry or some other chemical, electrical, or electrochemical process to measure the contaminant levels. Wire electrodes may be used to facilitate the tests. Unused portions of the electrode wires can be fed into the test chambers between tests to ensure clean and reliable electrodes for subsequent testing.

17 Claims, 14 Drawing Sheets

(56) References Cited

U.S. PATENT DOCUMENTS

| | | | |
|---|---|---|---|
| 4,058,446 | A | 11/1977 | Zirino et al. |
| 4,146,436 | A | 3/1979 | Kellermann et al. |
| 5,581,189 | A | 12/1996 | Brenn |
| 5,595,635 | A | 1/1997 | Clavell |
| 5,646,863 | A | 7/1997 | Morton |
| 5,686,829 | A | 11/1997 | Girault |
| 9,335,317 | B2 | 5/2016 | Matsubara et al. |
| 2003/0019748 | A1* | 1/2003 | Viltchinskaia ..... G01N 33/1813 204/400 |
| 2003/0173233 | A1 | 9/2003 | Vincent |
| 2007/0050157 | A1 | 3/2007 | Kahn et al. |
| 2007/0158211 | A1 | 7/2007 | Feng et al. |
| 2007/0179435 | A1* | 8/2007 | Braig ..................... A61B 5/145 604/66 |
| 2009/0123340 | A1 | 5/2009 | Knudsen et al. |

FOREIGN PATENT DOCUMENTS

| | | |
|---|---|---|
| CN | 203630085 U | 6/2014 |
| WO | WO 2006/043900 | 4/2006 |
| WO | WO 2012/120266 A1 | 9/2012 |

\* cited by examiner

AUTOMATED SMART WATER QUALITY MONITOR AND ANALYZER AND ASSOCIATED METHODS

CROSS REFERENCE TO RELATED APPLICATIONS

This application claims the benefit under 35 U.S.C. 119(e) to U.S. Provisional Application No. 62/363,135, filed Jul. 15, 2016, titled AUTOMATED IN-LINE SMART WATER QUALITY MONITOR AND ANALYZER. The entire content of the above-identified patent application is incorporated by reference herein and made a part of this specification. Any and all applications for which a foreign or domestic priority claims is identified in the Application Data Sheet as filed with the present application are hereby incorporated by reference under 37 CFR 1.57.

TECHNICAL FIELD

This application relates to devices and systems for analyzing and monitoring pollutant content in fluids.

DISCUSSION OF THE RELATED ART

Fluid testing systems often require considerably maintenance and operational costs, as the tests must be performed by a technician on-site. Additionally, many fluid testing systems utilize Hg and other hazardous materials in order to monitor the presence of contaminants in tested fluids. In some cases, fluid testing systems require regular maintenance and replacement of used electrodes.

SUMMARY

According to some variants, a fluid testing system that performs a plurality of test cycles on fluid can include a housing having an inlet and an outlet. The inlet can attach to a fluid line and the outlet can attach to the fluid line. In some embodiments, the system includes at least one testing chamber in the housing that receive fluid from the inlet of the housing. In some embodiments, the fluid testing system includes a fluid movement assembly that selectively directs fluid from the inlet into the at least one testing chamber. The system can include a wire feed system that provides first and second electrodes to the at least one testing chamber. In some embodiments, the wire feed system includes a length of first and second electrodes wires. In some embodiments, the wire feed system provides a new portion of the length of the first and second electrodes for each test cycle. The system can include a reference sample supply system that supplies reference samples to the at least one testing chamber. In some embodiments, the system includes a control system that controls the fluid movement assembly, the wire feed assembly and the reference sample supply system such that for each test cycle, the at least one testing chamber is filled with fluid and a new portion of the first and second electrodes are positioned into the at least one testing chamber. In some embodiments, the control system applies an electric signal to one electrode and samples the results on another so as to determine the presence of selected contaminants in the fluid in the at least one testing chamber.

In some embodiments, the control system for each testing cycle induces the delivery of the fluid to be tested, performs a first measurement by application of an electric signal to the first electrode, determines a first measurement indicative of the presence of a selected contaminant in at least one testing chamber by evaluating a signal received on a second electrode in response to the electric signal, then induces the supply of a known quantity of the selected contaminant to the at least one testing chamber and performs a second measurement by application of the electric signal to the first electrode and determines a second measurement indicative of the presence of the selected contaminant on the signal received on the second electrode in the at least one testing chamber.

In some embodiments, the control system determines the quantity of contaminant present in the at least one testing chamber by determining the difference between the first and second measurements.

In some embodiments, the wire feed system comprises at least one supply spool positioned within the housing and around which an unused quantity of at least one of the first and second electrode wires is wrapped, the wire feed system including an electrode movement apparatus configured to move an unused portion of each of the first and second electrodes into the at least one testing chamber after each test cycle is completed.

In some embodiments, the electrode movement apparatus comprises a collecting spool around which a portion of at least one of the first and second electrodes is wrapped.

In some embodiments, the system includes a motor configured to rotate the collecting spool, wherein the motor is controlled by the control system.

In some embodiments, the wire feed system is positioned in an electrode module configured to be removable from the housing.

In some embodiments, the electrode module includes a volume of fluid having a known concentration of a selected contaminant. In some embodiments, the electrode module is configured to output the volume of fluid into a constituent chamber in the housing separate from the electrode module when the electrode module is installed in the housing.

In some embodiments, the system includes a third electrode, wherein the first electrode is a working electrode, the second electrode is a counter electrode, and the third electrode is a reference electrode.

In some embodiments, the control system is configured to apply a positive voltage from the counter electrode to the working electrode, then to apply a negative voltage from the counter electrode to the working electrode, then to transition from the negative voltage back to the positive voltage, wherein the control system measures current and voltage relative to the reference electrode to determine an amount of at least one selected contaminant in the fluid in the testing chamber.

According to some variants, a fluid testing system that performs a plurality of test cycles on a fluid includes a housing having an inlet and an outlet. The inlet can be configured to attach to a fluid line and the outlet can be configured to attach to the fluid line. In some embodiments, the system includes at least one testing chamber in the housing that receives fluid from the inlet of the housing. In some embodiments, the system includes a first electrode and a second electrode. The fluid testing system can include a fluid supply system that supplies fluid samples to the at least one testing chamber, each fluid sample including a known concentration of at least one pollutant. In some embodiments, the fluid testing system includes a control system that controls the fluid sample supply system such that for each test cycle, the at least one testing chamber is filled with fluid. In some embodiments, the control system applies an electric signal to the first electrode and samples the results so as to determine the presence of selected contaminants in the fluid in the at least one testing chamber. In some embodiments, the control system induces the addition of a known amount of a selected contaminant to the at least one testing chamber and reapplies the electric signal and re-samples the results. In some embodiments, the results of the re-sampling are compared to the results of the sampling to determine the amount of the selected contaminant in the fluid.

In some embodiments, the fluid testing system includes a wire feed system that provides the first and second electrodes to the at least one testing chamber, wherein the wire feed system includes a length of first and second electrodes wires and wherein the wire feed system provides a new portion of the length of the first and second electrodes for each test cycle, and wherein the control system is configured to control operation of the wire feed system.

In some embodiments, the fluid testing system include a wired or wireless signal generator in electrical communication with the control system, wherein the wireless signal generator generates wireless signals including the results of the sampling on the second electrode.

In some embodiments, the fluid testing system includes a unique identifier, wherein the unique identifier is used to correlate the results sampled by the control system with the physical location of the system.

In some embodiments, the control system is configured to operate via remote control and/or by preset automated control.

In some embodiments, the signal generator is positioned within the housing.

A method of measuring levels of one or more pollutants in a fluid can include passing a test volume of fluid through an inlet of a housing into a test chamber within the housing. In some embodiments, the method includes adding a predetermined volume of acid to the test chamber. The method can include introducing a first test length of a first electrode wire into the test volume. In some embodiments, the method includes introducing a first test length of a second electrode wire into the test volume. The method can include introducing a first test length of third electrode wire into the test volume. In some embodiments, the method includes applying a positive voltage from the third electrode to the first electrode for a first period of time. The method can include applying a negative voltage from the third electrode to the first electrode for a second period of time. In some embodiments, the method includes transitioning from the negative voltage back to the positive voltage over a third period of time. In some embodiments, the method includes measuring current and voltage in the fluid in the test chamber relative to the second electrode. The method can include, after the measuring step, adding a known quantity of fluid having a known concentration of a selected pollutant to the test chamber and then repeating the applying, transitioning, and measuring steps. In some embodiments, the method includes determining an amount of the selected pollutant in the test volume of fluid by comparing the measured currents and voltages from before and after the adding of the known quantity of fluid having a known concentration of the selected pollutant.

In some embodiments, the method includes moving the first test length of first electrode wire out from the test volume and moving a second test length of first electrode wire into the test volume, the second length connected to the first length. The method can include moving the first test length of second electrode wire out from the test volume and moving a second test length of second electrode wire into the test volume, the second length connected to the first length. In some embodiments, the method includes moving the first test length of third electrode wire out from the test volume and moving a second test length of third electrode wire into the test volume, the second length connected to the first length. In some embodiments, the moving steps are performed by an electrode transition mechanism configured to selectively move the first, second, and third electrodes through the test volume In some embodiments, the determining step is performed before the moving steps.

In some embodiments, the first electrode is a working electrode, the second electrode is a reference electrode, and the third electrode is a counter electrode.

In some embodiments, the step of transitioning from the negative voltage back to the positive voltage is performed using a square wave or differential wave superimposed on a linear voltage increase or stepped voltage increase.

BRIEF DESCRIPTION OF THE DRAWINGS

The present inventions are described with reference to the accompanying drawings, in which like reference characters reference like elements, and wherein.

DETAILED DESCRIPTION

Figure 1:
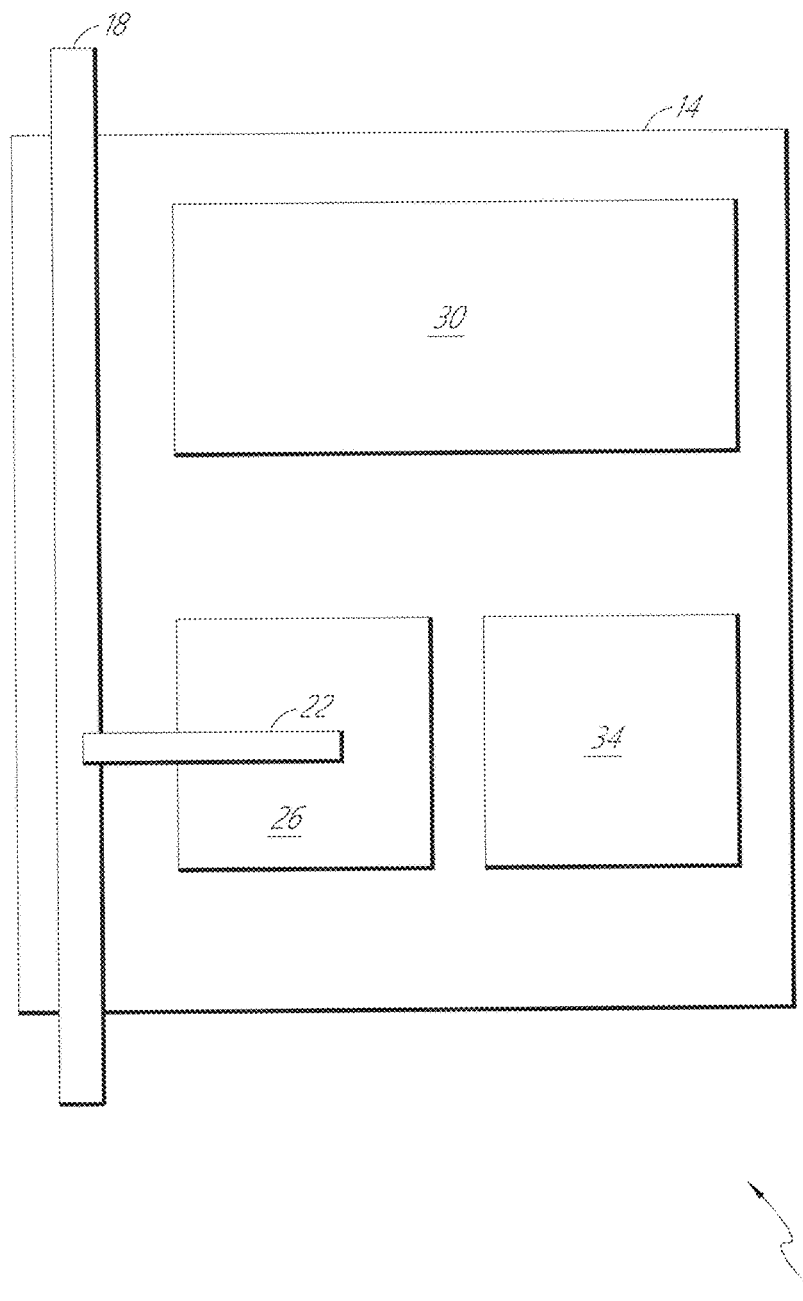
FIG. 1 is schematic representation of a fluid testing system.

The apparatuses, systems, and methods described herein is designed to include various detecting modules as explained in detail below, take fluid samples directly from a pipeline or other fluid line (e.g. a main water line of a residential, commercial, or municipal building(s), water treatment lines, urban water lines, rural water lines, and/or any other water or fluid line for which contaminant analysis is desired), and perform quantitative analysis of certain contaminants present in the water or other fluid samples. The systems and apparatuses can be positioned at the inlet (and/or upstream) or outlet (and/or downstream) of the target sampling site. In some applications, the systems and apparatuses are used to analyze contaminants present in lakes, water tanks, containers, and/or other non-flowing water or fluid environments. In some such cases, the apparatus and systems can include pump or other fluid flow mechanisms configured to move fluid into and out from the fluid testing apparatus/system. The analyzed fluid samples can be collected in a common storage chamber. The data from the apparatus can be wirelessly transmitted via communication methodologies (e.g. Wi-Fi, Bluetooth, Radio, Satellite, Cellular and others) and stored using cloud data management techniques. In some configuration, the data, or some portion thereof, is transferred via a wired connection. The complete detection, transmission, monitoring, and analysis of the data may be built into a data server, database or a computer device as a comprehensive software stack with all the analysis and location mapped correlation metrics presented to the user.

The detecting modules of the apparatus are capable of detecting and quantifying ions in water samples using methods such as, for example, ASV (Anodic Stripping Voltammetry) and its derivatives including; squarewave, differential pulsed, cathodic stripping voltammetry, constant current stripping voltammetry, and/or other combinations or modifications of ASV methods. The ionic content of sampled water is quantitatively analyzed, the information stored and transmitted to an aggregation device (e.g., a phone, computer, dedicated monitor, etc.). The ionic analysis uses electrodes made of Au, Bi, Al, Ga, In. Sn, Sb, Ir and Ir-oxide, Graphene/Graphite, and/or other materials or combinations of materials such as BiSn, BiSb, InSb, and other alloys. Preferably, the devices (e.g., the electrodes) of the present disclosure are configured to operate without use of Hg, Pb, Cd, Cr, and other toxic/unstable materials. Given the toxicity of these materials, and the health risks they pose, it is desirable to avoid using these materials. The devices and systems of the present disclosure can be capable of operating in one or more of the following manners: (1) using wire electrodes whose lengths can be fed through the sample chamber between testing cycles to introduce new, clean electrodes; (2) re-using the substrate material and plating a thin film or the electrode onto the substrate concurrently with the analyte; (3) using replaceable, pre-manufactured electrodes consisting of the substrate and electrode material, which are automatically dispensed and replaced in the sample; and/or (4) using an automated, internal polishing mechanism consisting of a rotary or linear brush used to clean the surface of the disposable electrode.

Using these methods, Pb, As, Cd, Hg, Cr, Mn, and other elements present in water as ionic species can be detected precisely and accurately down to low concentrations (e.g., less than 20 ppb (parts-per-billion), less than 10 ppb, less than 5 ppb, less than 2 ppb, and/or less than 1 ppb). One or more of these methods of operation may be used in tandem. In some embodiments, the apparatus will be automated in addition to or instead of remote controlling the initiation of measurement sequences (outside or scheduled measurements). In some embodiments, the data will be wirelessly transmitted and analyzed.

FIG. 1 illustrates a schematic representation of a fluid testing system 10. The system 10 can include a housing 14. The housing 14 can be configured to be integrated in-line with a fluid line 18 (e.g., a water pipe or other fluid conduit). In some configurations, a pump or other fluid flow mechanism can be used to pull fluid from a tank, reservoir, or other stationary fluid source. A fluid diverter 22 can fluidly connect a test chamber 26 with the fluid line 18. The fluid diverter 22 can be configured to selectively direct fluid from the fluid line 18 to the test chamber 26. A fluid testing system 30 can be positioned at least partially within the housing 14 to perform testing of the fluid in the test chamber. The fluid testing system 30 can include one or more electrodes, pumps, electrical signal generators, and other electrical, mechanical, and/or chemical components configured to be used to measure contaminant content in the tested fluid. Preferably, the fluid testing system 30 includes one or more structures for moving fluids between chambers inside or and/or outside of the housing 14. A control system 34 can be positioned in or near the housing 14. The control system 34 can be configured to control operation of the various components of the fluid testing system 30, test chamber, fluid diverter 22, and other components to facilitate tests and testing cycles on the fluid in the test chamber 26. The control system 34 can be controlled by a remote user via wireless and/or wired communication. In some cases, the control system 34 is at least partially controlled via preset algorithms and commands. The system 10 can be configured to be installed in a water line or other fluid system and then operated remotely. Such configurations can reduce operational costs and facilitate more frequent testing, as on-site personnel would not be needed for the daily operation of the system 10.

Figure 2:
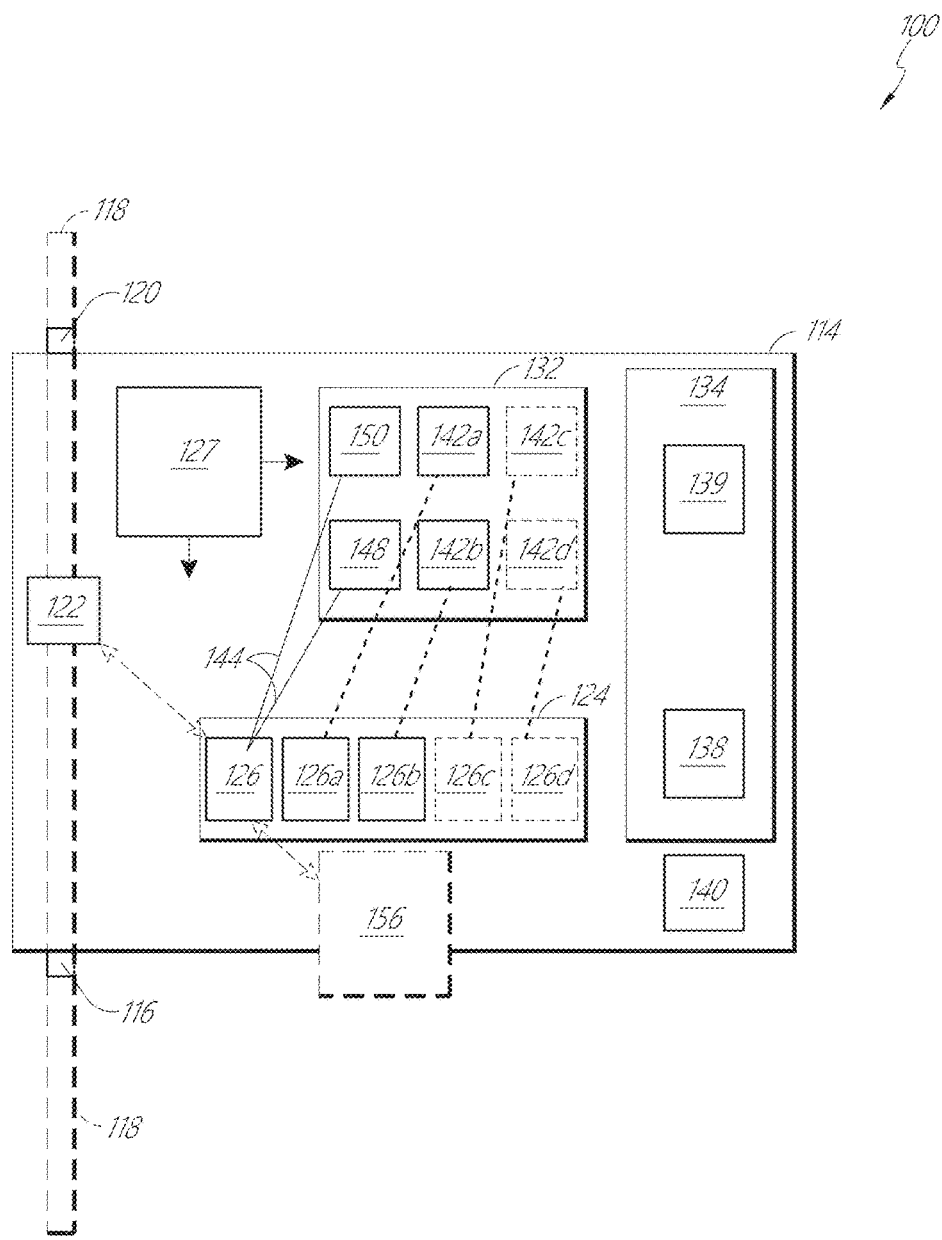
FIG. 2 is a schematic representation of another fluid testing system.

FIG. 2 illustrates a schematic representation of a fluid testing system 100. As illustrated, the fluid testing system 100 includes a housing 114. The housing 114 has an inlet 116 configured to connect to a fluid line 118. The housing 114 can include an outlet 120 configured to connected to the fluid line 118 downstream of the system 100. As illustrated, the fluid testing system 100 can be positioned "in-line" with the fluid line 118. Preferably, the system 100 can be installed in-line with the fluid line 118 without requiring a bypass fluid line or other significant structural changes to the fluid system being tested. In some applications, the inlet 116 and/or outlet 120 of the housing 114 are fluidly connected to a stationary fluid source to be tested. In some embodiments, the inlet 116 and outlet 120 of the housing are on opposite sides of the housing 114 from each other. In some embodiments, the inlet 116 and outlet 120 are on the same side of the housing 114. In some embodiments, the inlet 116 and outlet 120 are on different, non-opposite sides from each other.

The fluid testing system 100 can include a chamber assembly 124. The chamber assembly 124 can include a plurality of chambers configured to hold various types and volumes of liquids, powders, or other materials. The chambers can be positioned near each other within the housing 114. In some embodiments, one or more chambers are positioned in a location remote from one or other chambers within or outside of the housing 114.

A fluid transfer mechanism 127 can be positioned at least partially within the housing 114. The fluid transfer mechanism 127 can be configured to transfer fluid between various volumes within the fluid testing system 100. For example, the fluid transfer mechanism 127 can move fluid between the one or more chambers in the chamber assembly 124. In some embodiments, the fluid transfer mechanism 127 includes a sensor or monitor configured to measure the volume of fluid within various chambers and containers in the fluid testing system 100. The fluid transfer mechanism 127 can include one or more moving parts configured to travel between chambers and containers within the fluid testing system 100. In some embodiments, the fluid transfer mechanism 127 includes one or more fluid lines, valves, pumps, and/or other fluid transfer components configured to move fluid from one volume to another.

As illustrated in FIG. 2, the fluid testing system 100 can include a testing module 132. The testing module 132 can include one or more mechanisms configured to facilitate testing of the fluid in the chamber assembly 124. Preferably, the testing module 132 is self-contained. For example, the testing module 132 can be configured to be connected and disconnected from the housing 114 with little or no modification or disassembly/reassembly of the testing module 132.

The fluid testing system 100 can include a flow diverter 122. The flow diverter 122 can be positioned in the fluid path between the inlet 116 and outlet 120 of the housing 114. The flow diverter 122 can be configured to divert flow from the fluid line 118 to the chamber assembly 124. For example, the flow diverter 122 can include one or more valves, pumps, and/or other fluid mechanical mechanisms configured to facilitate flow of test fluid (e.g., the fluid to be tested by the system 100) to the chamber assembly 124. In some applications, the valve, pumps, and/or other fluid mechanical mechanisms are used to draw fluid from a stationary test site (e.g., a lake, reservoir, tank, etc.). In some embodiments, the flow diverter 122 relies on line pressure in the fluid line 118 to drive fluid to the chamber assembly 124. Such a configuration can reduce the amount of power required to move fluid to the chamber assembly 124, as compared to systems in which pumps or other powered mechanisms are used to move the test fluid. In some embodiments, the flow diverter 122 includes one or pumps or other mechanisms configured to move fluid from the fluid line 118 and/or stationary fluid site to the chamber assembly 124.

The fluid testing system 100 preferably includes a control system 134. The control system 134 can positioned partially or entirely within or on the housing 114. The control system 134 can be configured to control varies subsystems and components of the fluid testing system 100. For example, the control system 134 can control the flow diverter 122, fluid transfer mechanism 127, testing module 132, and/or other components of the fluid testing system 100. In some embodiments, the control system 134 includes a wireless or wired communication device 138. The communication device 138 can be configured to send and/or receive signals to one or more components of the fluid testing system 100 and/or to remote components (e.g., the hubs discussed below, and/or a network of distributed servers). A battery 140 or other power source can be positioned within or near the housing 114 can configured to power one or more of the components of the housing. The control system 134 can include one or more processors 139, circuit boards, and/or other electronic components.

With continued reference to FIG. 2, the chamber assembly 124 can include a test chamber 126. The test chamber 126 can be configured to receive test fluid from the fluid line 118. In some embodiments, the chamber assembly 124 includes a second chamber 126a separate from the test chamber 126. The second chamber 126a can be configured to hold an electrolyte for use in an ASV analysis of the test fluid. The chamber assembly 124 can include one or more chambers in addition to the test chamber 126 and second chamber 126a. For example, the chamber assembly 124 can include a third chamber 126b configured to hold a fluid having known concentrations of contaminants of interest (e.g., lead, cadmium, chromium, arsenic, and their ionic species, etc.). The chamber assembly 124 can include additional chambers 126c, 126d configured to hold additional fluids or other substances (e.g., contaminants, powders, water, etc.).

The testing module 132 can include one or more fluid chambers 142a, 142b, 142c, 142d (collectively 142). The fluid chambers 142 can be configured to hold fluids such as, for example, electrolytes, fluids with known concentrations of contaminants, water, acids, and/or other fluids. In some embodiments, the fluid chambers 142 are configured to output fluid into the chambers 126a, 126b, 126c, 126d of the chamber assembly 124 when the testing module 132 is connected to the housing 114. Fluid lines (e.g., the dashed lines in FIG. 2) can be established between the fluid chambers 142 of the testing module 132 and the chambers of the chamber assembly 124 when the testing module 132 is coupled with the housing 114. In some embodiments, the fluid chambers 142 include release valves configured to open and allow fluid transfer to the chamber assembly 124 when the testing module 132 is coupled with the housing 114. The fluid chambers 142 can be configured to provide a sufficient amount of fluid and/or other materials to the fluid testing system 100 to facilitate ASV or other tests for a predetermined period of time (e.g., at least 1 month, at least 6 months, at least 1 year, and/or at least 3 years). In some embodiments, the fluid chambers 142 are fluidly connected to the testing chamber 126 when the testing module 132 is coupled with the housing 114. In some such arrangements, valves, pumps, solenoids, and/or other fluid flow control mechanisms can be positioned in the fluid path(s) between the fluid chambers 142 and the testing chamber 126. In some such embodiments, precise input of fluids from the fluid chambers 142 into the test chamber 126 may be accomplished without a fluid transfer mechanism 127 (e.g., a moveable fluid transfer mechanism).

As will be described in more detail below, the testing module 132 can include at least one electrode 144. The at least one electrode 144 can be positioned at least partially within one or more chambers of the chamber assembly 124 when the testing module 132 is coupled with the housing 114. For example, the at least one electrode 144 can be positioned at least partially within the test chamber 126. In some embodiments, an electrode frame or other structure extends the at least one electrode 144 into the test chamber 126 when the testing module 132 is coupled with the housing 114.

In some embodiments, the at least one electrode 144 is a wire (e.g., a coated wire or solid wire). The testing module 132 can include an electrode source 148. The electrode source 148 can be, for example, a spool around which electrode wire is wrapped. The testing module 132 can include an electrode collector 150. The electrode collector 150 can be a spool configured to turn to pull the at least one electrode 144 through the test chamber 126. In some embodiments, the electrode source 148 is configured to supply a sufficient length of electrode wire to facilitate ASV or other tests for a predetermined period of time (e.g., at least 1 month, at least 6 months, at least 1 year, and/or at least 3 years).

The fluid testing system 100 is configured such that testing modules 132 having varied features and/or testing parameters can be exchanged from the housing 114 as needed. For example, testing modules 132 having different fluids within the fluid chambers 142 can be exchanged based on the target contaminants to be tested in a given application. In some cases, testing modules 132 having different constructions/operable components can be exchanged in the housing 114. For example, a testing module 132 designed to measure pH of the fluid in the test chamber 126 may include a probe configured to measure pH of the fluid. The probe can be connected to the testing module 132 and can extend into the testing chamber 126 when the testing module 132 is connected to the housing 114. The pH probe can be included in addition to or instead of the electrodes 144 described above. In some embodiments, the pH probe includes a liquid, gel, or polymer electrolyte. The probe can include a wire (e.g., a platinum wire or other suitable wire) and a frit (e.g., a glass or plastic frit). Such a construction can allow exchange between ions in the probe and hydrogen ions in the sample fluid in the test chamber 126. This exchange can create a potential difference across the frit which can be measured to determine the pH level of the test fluid. In some applications, the pH testing module 132 can include a reference electrode (e.g., a wire positioned in a silver:silver-chloride solution) against which the potential measurements across the frit can be compared. In some applications, a testing module 132 can be configured to measure turbidity the test fluid. For example, the testing module 132 can include a light source and a light sensor. The light can be passed through the test fluid and measured by the sensor after passage through the fluid. In some configurations, one or more of the light source and light sensor are built into the housing 114 separate from the testing module 132. In some applications, the test chamber 126 includes one or more reflective surfaces used to reflect light from the light source to the light sensor. In some applications, one or both the light source and light sensor are immersed in the test fluid in the test chamber 126. In some configurations, the testing module 132 can be configured to measure temperature of the test fluid. For example, IR thermometers, thermocouples, or other temperature measurement mechanisms can be included with the testing module 132 or housing 114. These temperature measurement mechanisms can operate in conjunction with or instead of the other measurement mechanisms and methods described herein (e.g., ASV, pH, turbidity, etc.).

As illustrated in FIG. 2, the fluid testing system 100 can include a waste container 156. The waste container 156 can be positioned inside, partially within, or outside of the housing 114. Preferably, upon completion of a test cycle (described in detail below), fluid from one or more of the test chamber 126 and/or other chambers 126a, 126b, 126c, 126d is outlet to the waste container 156. For example, upon completion of a test cycle, fluid from the test chamber 126 can be output to the waste container 156. The fluid testing system 100 can include a heater configured to heat the contents of the waste container 156 (e.g., to a temperature between 30-70☐, 40-80☐, 35-65☐, and/or 50-60☐). Heating the contents of the waste container 156 can accelerate evaporation of the fluid in the waste container 156.

FIGS. 3-8 illustrate an embodiment of a fluid testing system 200 that can have components or portions that are the same as or similar to the components or portions of other systems described herein. More specifically, the fluid testing system 200 can share many of the characteristics of the fluid testing system 100 described above. Like numbers, wherein the value is increased by 100, are used to describe features that share all or many structural and functional features between the systems 100 and 200. For example, the fluid chambers 242a, 242b, 242c can have the same structure and function as the fluid chambers 142a, 142b, 142c described above (e.g., they are each configured to fluidly connect with a respective chamber 226a, 226b, 226c in the chamber assembly 224).

Figure 3:
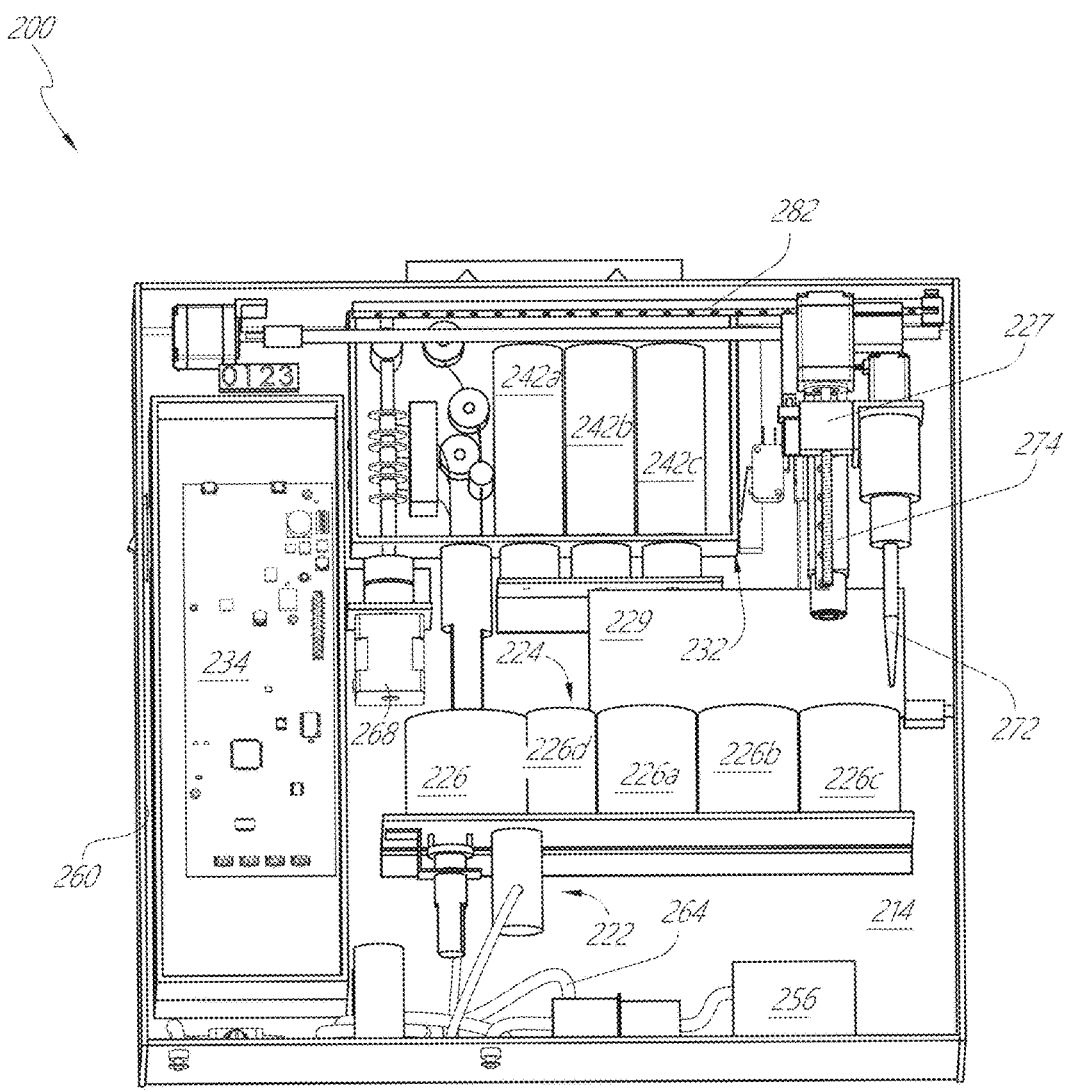
FIG. 3 is a front view of an embodiment of a fluid testing system.
Figure 3A:
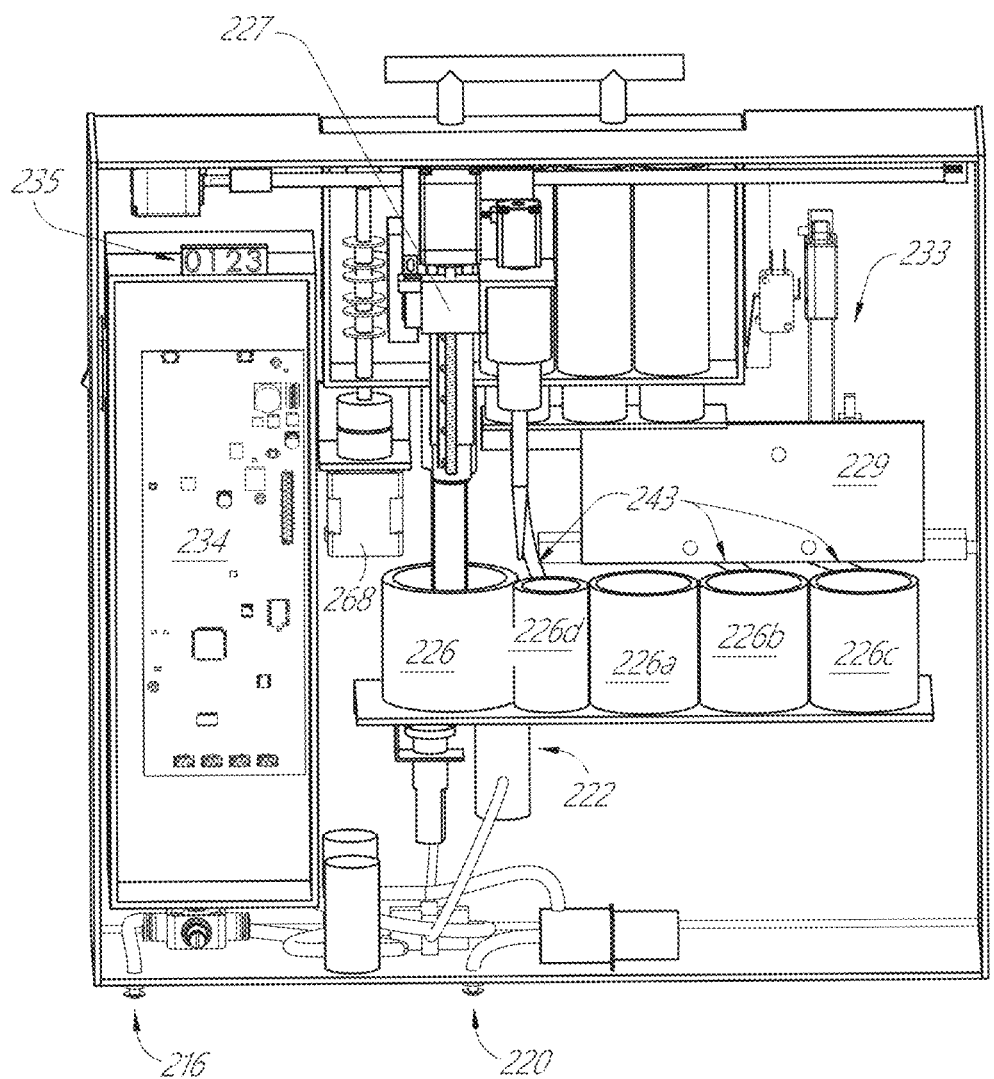
FIG. 3A is a front view of the fluid testing system of FIG. 3, wherein the fluid transfer system is shifted to the opposite side of the housing and the testing module is removed.

As illustrated in FIG. 3, the control assembly 234 can be positioned within an enclosure 260. The enclosure 260 can be configured to fluidly isolate the control assembly 234 (e.g., the circuit boards, signal processors, and other electronic components) from other components in the fluid testing system 200. For example, the enclosure 260 can reduce or eliminate exposure of the control assembly 234 to unintentional fluid contamination from the chambers 242a, 242b, 242c, 226, 226a, 226b, 226c, and 226d. In some embodiments, the fluid testing system 200 includes a panel 229 positioned within the housing 214. The panel 229 can function as a lid, cap, and/or seal for one or more of the chambers 226, 226a, 226b, 226c, 226d of the chamber assembly 224. As illustrated in FIG. 3A, the panel 229 can be operated by an actuator 233. The actuator 233 can be, for example, a step motor, a pneumatic mechanism, a hydraulic mechanism, another electromechanical mechanism and/or some combination thereof. The actuator 233 can be configured to tilt, rotate, translate, or otherwise move the panel 229 between an offset position (illustrated in FIG. 3A) and a covering position wherein the panel covers the open ends of one or more of the chambers of the chamber assembly 224. The operation of the actuator 233 and panel 229 can be controlled by the control assembly 234.

The control assembly 234 can include a display 235. The display 235 can include a digital and/or analogue screen. In some embodiments, the display 235 is configured to indicate one or statuses of the fluid testing system 200. For example, the display 235 can indicate the power status (e.g., ON/OFF, battery life, etc.), the operational status (e.g., active testing, passive power, etc.), error messages (e.g., associated with failure of one or more components), and/or other status messages.

Referring to FIG. 3, the flow diverter 222 can be connected to the test chamber 226. As illustrated, the flow diverter 222 can comprise one or more solenoids, pumps, and/or fluid lines. The solenoids illustrated in FIG. 3 can be used to open and close fluid communication between the fluid line 218 and the components of the chamber assembly 224. For example, solenoids can be controlled by the control assembly 234 to open and close fluid communication between the fluid line 218 and the test chamber 226. In some embodiments, the flow diverter 222 or some other mechanism is used to open and close fluid communication between the chamber assembly 224 and the waste container 256. A pump or other fluid flow mechanism can be used to pull fluid into the test chamber 226 from a test fluid source (e.g., a stationary source). The flow diverter 222 and/or test chamber 226 can be fluidly connected to the waste container via a fluid line (e.g., tube) 264.

Figure 4:
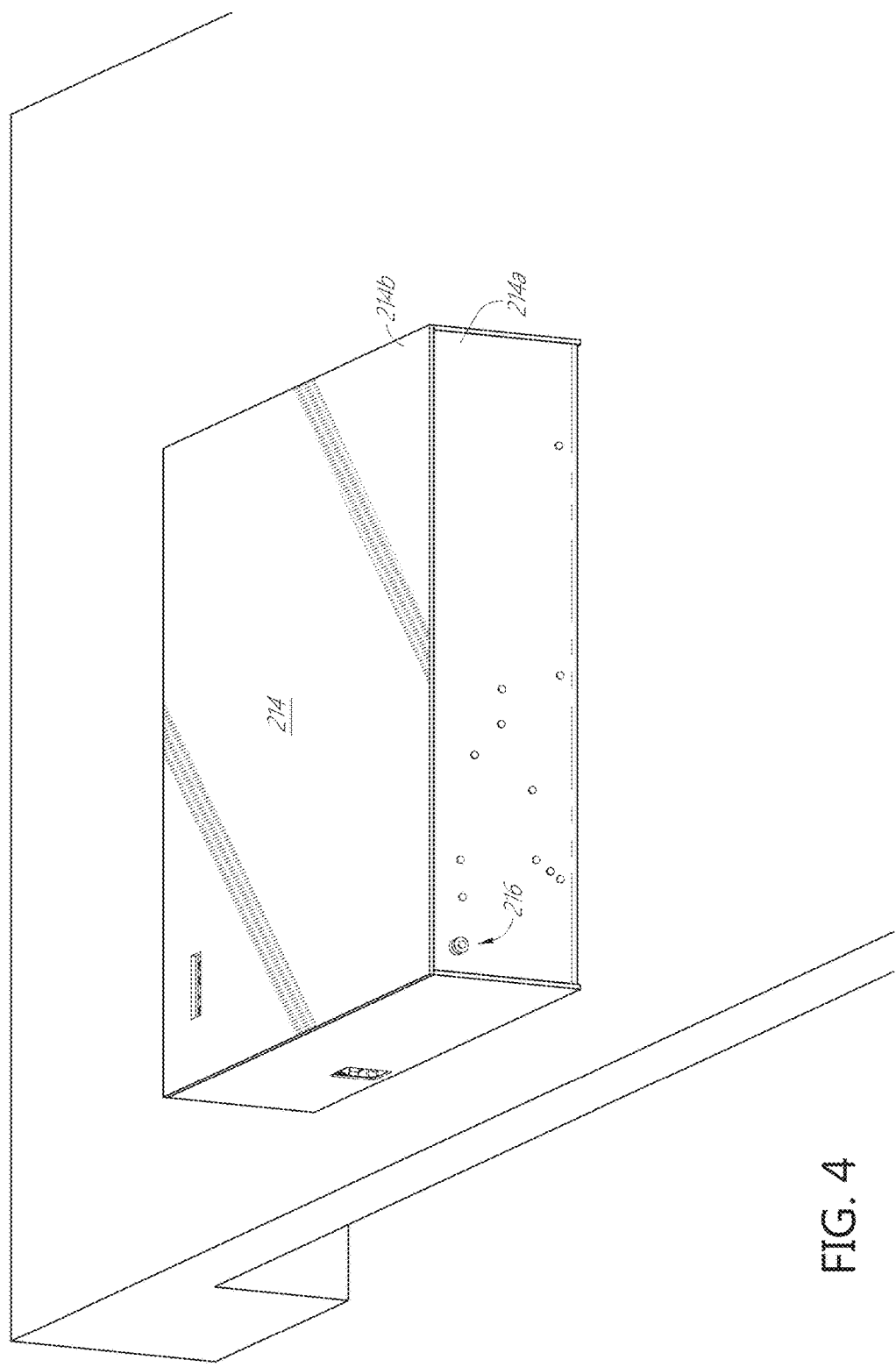
FIG. 4 is a bottom perspective view of the housing of the fluid testing system of FIG. 3.

As illustrated in FIG. 4, the housing 214 can have a generally rectangular prism shape. Other shape, including cylinder, cones, pyramids, or other 3-dimensional shapes could also be utilized. The housing 214 can be constructed from a metal, polymer, ceramic, glass, or some combination thereof. As illustrate, the housing 214 can be constructed from aluminum. The housing 214 can be fluid resistant in order to reduce exposure of the internal components of the system 200 to outside moisture, debris, and other environmental factors. In the illustrated embodiment of FIG. 4, the inlet 216 is illustrated as being positioned on the bottom 214a of the housing 214. As illustrated in FIG. 3A, the outlet 216 may also be positioned on the bottom 214a of the housing 214, though other positions are also possible. A front side 214b of the housing 214 can be removed to provide the view of the internal components provided in FIG. 3. In some embodiments, the overall size of the housing 214 can be small. For example, the front side 214b of the housing 214 can be less than 20"×20" in size. In some cases, the front side 214b of the housing is less than 10"×10". In some embodiments, the front side 214b is approximately 15"×16". Many sizes are possible. In some embodiments, the bottom side 214a is approximately 16"×9", though many other sizes, both smaller and larger are possible. In some applications, the housing 214 is sized to be used in a house, apartment, condominium, and/or other residential property.

Figure 5:
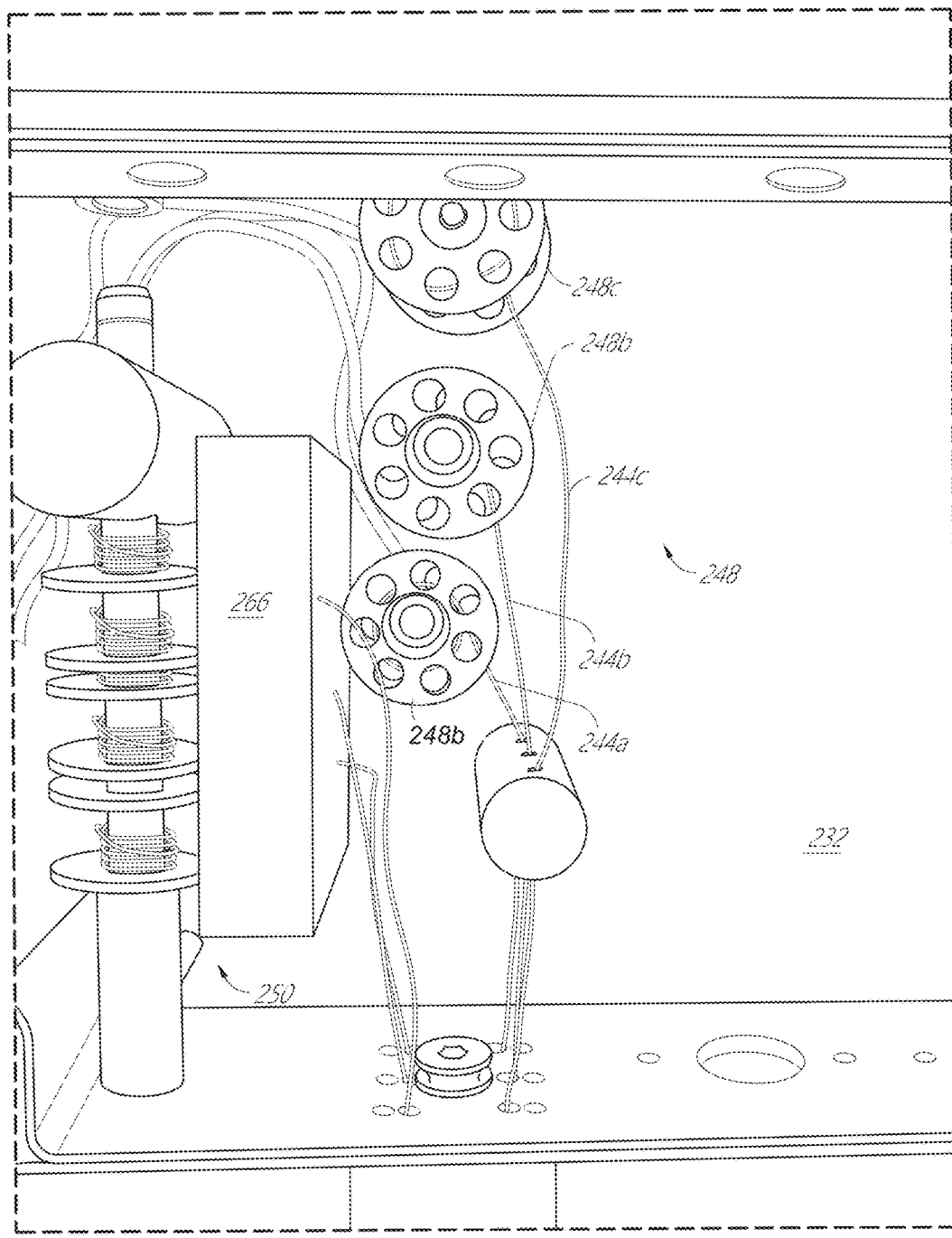
FIG. 5 is a front view of a testing module of the fluid testing system of FIG. 3.

FIG. 5 illustrates an embodiment of the electrode wires, electrode sources, and electrode collectors. As illustrated, the electrode can comprise a plurality of electrode wires. For example, the electrode can include a first wire 244*a*, a second wire 244*b*, and a third wire 244*c*. Each of the wires 244*a*, 244*b*, 244*c* can be wrapped around a respective source spool 248*a*, 248*b*, 248*c*. An opposite end of each electrode wire 244*a*, 244*b*, 244*c* can be wrapped around respective spools on the electrode collector 250. In some embodiments, the testing module 232 includes an alignment feature 266 (e.g., a block with apertures, grooves, or some other alignment feature). The alignment feature 266 can be configured to reduce the risk that the respective electrode wires entangle each other. For example, the one or more electrodes can pass through apertures in the alignment features 266. The electrode collector 250 can be connected to a motor 268 (FIG. 3) or other source of rotational actuation. In some embodiments, insertion of the testing module 232 into the housing 214 operably couples the electrode collector 250 to the motor 268.

Figure 6:
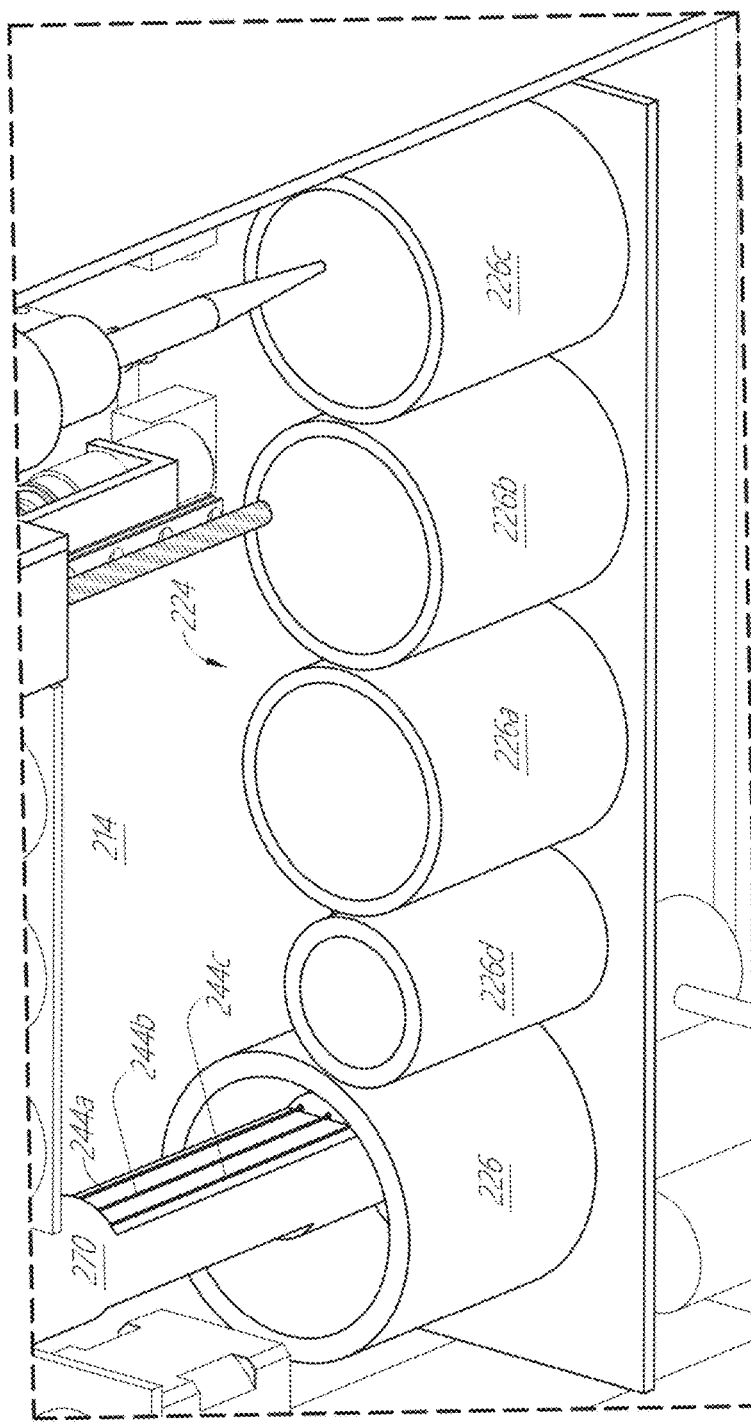
FIG. 6 is a top perspective view of a chamber assembly of the fluid testing system of FIG. 3.
Figure 7:
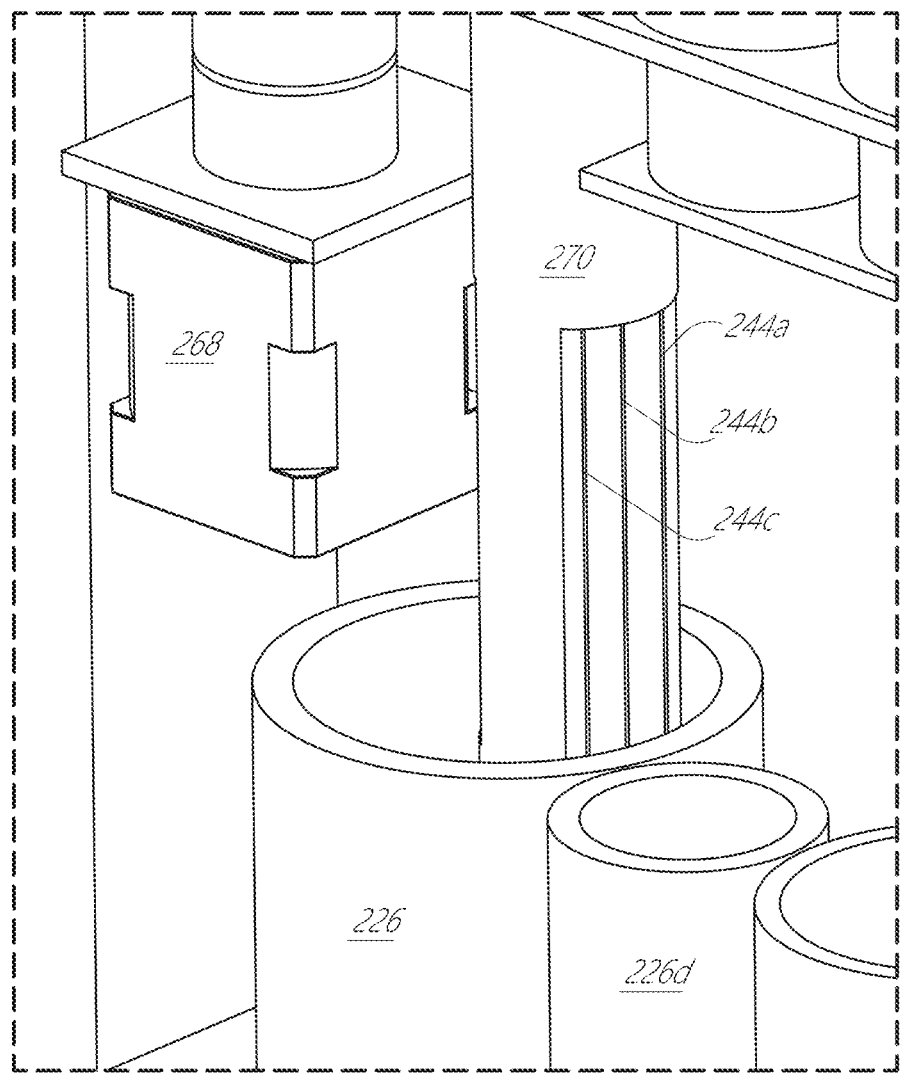
FIG. 7 is a top perspective view of portion of the chamber assembly of the fluid testing system of FIG. 3.

As illustrated in FIGS. 6-7, the testing module 232 can include an electrode guide 270. The electrode guide 270 can be configured to position at least a portion of each of the electrodes within the test chamber 226 when the testing module 232 is coupled with the housing 214. In some embodiments, the electrode guide 270 includes an elongate body projecting out from the testing module 232 (e.g., projecting downward from the module 232). The electrode guide 270 can include one or more apertures, grooves, or other features at or near the end of the electrode guide opposite the testing module and configured to maintain the electrode wires separate from each other within the test chamber 226.

Figure 8:
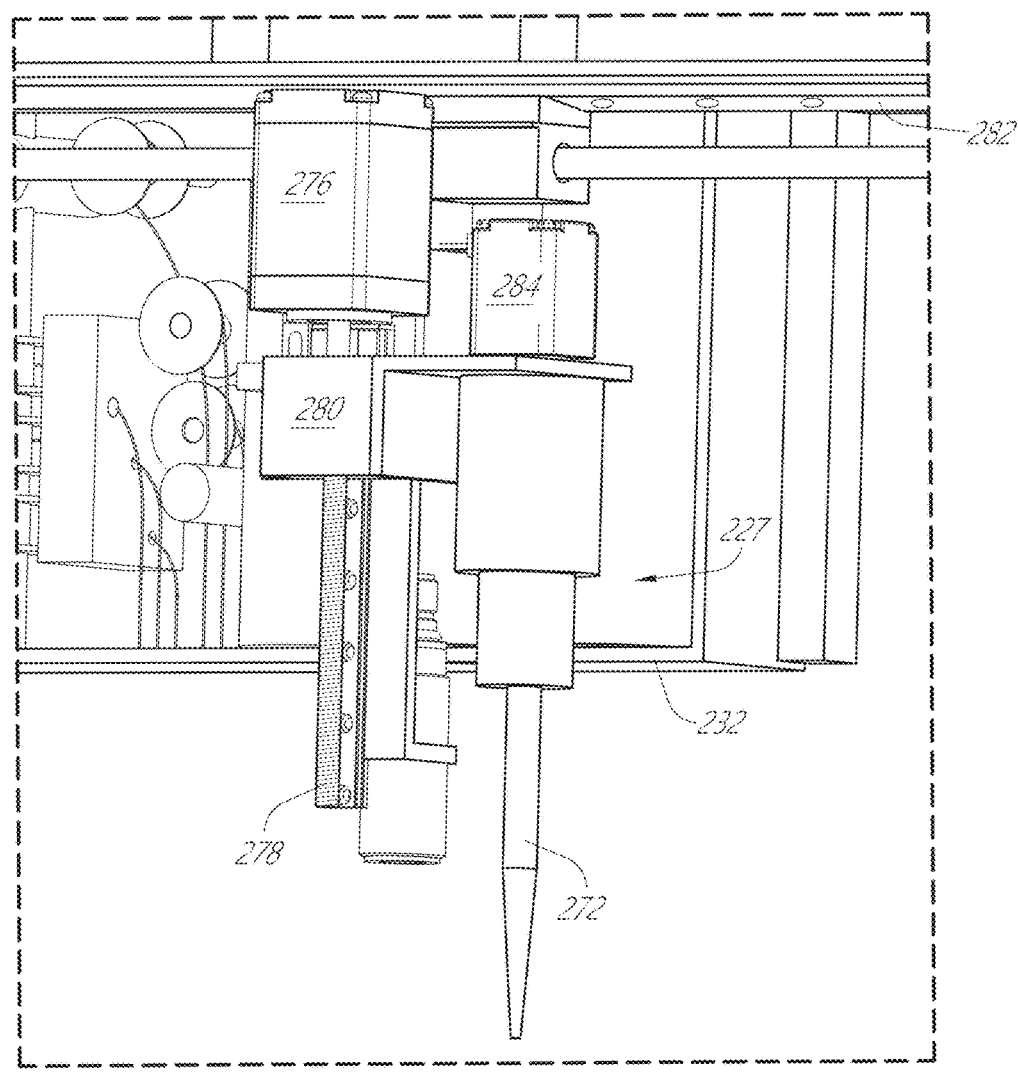
FIG. 8 is a front view of a fluid transfer mechanism of the fluid testing system of FIG. 3.

As illustrated in FIG. 8, the fluid transfer mechanism 227 can include a fluid intake portion 272. The fluid intake portion 272 can be configured to collect fluid from one of more of the chambers 226, 226*a*, 226*b*, 226*c*, 226*d* and deposit that fluid in another of the chambers. In some embodiments, the fluid intake portion 272 is configured to selectively move fluids in a very precise manner (e.g., on the order of microliters). The fluid intake portion 272 can be, for example, a pipette, a syringe, or some other structure configured to collect and release fluid.

In some embodiments, the fluid transfer mechanism 227 or some other portion of the fluid testing system 200 includes a sensor 274 (FIG. 3) configured to measure the volume of fluid within one or more of the chambers 226, 226*a*, 226*b*, 226*c*, 226*d*. The sensor 274 can be, for example, an ultrasonic sensor or other sensor configured to detect fluid height within the chambers 226, 226*a*, 226*b*, 226*c*, 226*d*. The fluid volume can then be calculated by the control system 234 or some other component based upon the cross-sectional area of the respective chambers.

The fluid transfer mechanism 227 can include a movement system. The movement system of the fluid transfer mechanism 227 can be configured to move the fluid intake portion 272 and/or sensor 274 in at least one direction of movement. For example, as illustrated, the fluid transfer mechanism 227 can include a motor 276 configured to rotate a drive screw 278. The fluid intake portion 272 and/or sensor 274 can be connected to a frame 280 or other structure configured to move parallel to the longitudinal axis of the screw 278 as the screw 278 is rotated. As illustrated, the longitudinal axis of the screw 278 can be aligned parallel or substantially parallel to vertical and/or perpendicular or substantially perpendicular to the top surfaces of fluid within the chambers 226, 226*a*, 226*b*, 226*c*, 226*d*. In some embodiments, the fluid transfer mechanism 227 is configured to ride on a guide rail 282 that extends in a direction perpendicular or oblique to the longitudinal axis of the drive screw 278. Movement of the fluid transfer mechanism 227 along the guide rail 282 can be controlled by a second motor 284. In some embodiments, movement of the fluid transfer mechanism 227 along the guide rail 282 brings the intake portion 272 and/or sensor 274 into alignment with the various chambers 226, 226*a*, 226*b*, 226*c*, 226*d*.

In some configurations, the fluid transfer mechanism 227 can be positioned in front of or behind (e.g., offset in the direction perpendicular to both the drive screw 278 and guide rail 282) the testing module 232 when the testing module 232 is coupled with the housing 214. Such an arrangement can help to reduce the overall size of the housing 214.

A method of testing fluid using the fluid testing system 200 can include diverting a portion of test fluid from the fluid line to the test chamber 226. In some configurations, test fluid is also diverted to a secondary chamber 226*d*. The secondary chamber 226*d* can be fluidly connected to the test chamber 226 while test fluid is diverted to the chambers. In some embodiments, a valve between the test chamber 226 and the secondary chamber 226*d* is closed when diversion of test fluid to the test chamber 226 is ceased.

In some embodiments, the amount of test fluid diverted to the test chamber 226 is measured via measurement and/or control of pressure in the diverted test fluid and to determine the flow rate of fluid into the test chamber 226. This flow rate can be compared to the amount of time spent diverting fluid to the test chamber 226 to determine the volume of test fluid within the test chamber 226. In some embodiments, the sensor 274 is used to measure the volume of test fluid within the test chamber 226.

Before or after diversion of test fluid into the test chamber 226, the testing module 232 can be coupled with the housing 214. When the testing module 232 is coupled to the housing 214, preloaded fluids in the chambers 242*a*, 242*b*, 242*c* can be directed to the chambers 226, 226*a*, 226*b*, 226*c* in the chamber assembly 224. For example, chamber 242*a* can hold an electrolyte solution (e.g., hydrochloric acid) that is transferred to an electrolyte chamber 226*a* for use in the testing of the test fluid. The chambers 242*b*, 242*c* can include fluids with known concentrations of one or more contaminants of interest. These contaminants can include, but are not limited to lead, arsenic, cadmium, zinc, manganese, chromium, copper, chlorine, iron, fluorides, chlorides, or some combination thereof. The chambers 242*b*, 242*c* can divert their respective fluids to chambers 226*b*, 226*c*, respectively. Transfer of fluids from the chambers 242 to the chambers 226 can be facilitated via opening of valves in the chambers 242. In some embodiments, pumps or other fluid transfer devices can be used to direct fluid between the chambers. In some embodiments, fluid is transferred to the chambers 226 under the force of gravity without use of additional fluid transfer devices. Fluid lines 243 (FIG. 3A) can connect each of the respective chambers 242 to the chambers 226.

The method of testing the test fluid can include using the fluid transfer mechanism 227 to transfer electrolyte from the electrolyte chamber 226*a* to the test chamber 226. An agitator (e.g., a paddle wheel, magnetic stir bar, or other structure configured to agitate or stir the fluid in the test chamber 226) can be operated to evenly distribute the constituents of the test fluid and electrolyte in the test chamber 226.

Figure 9:
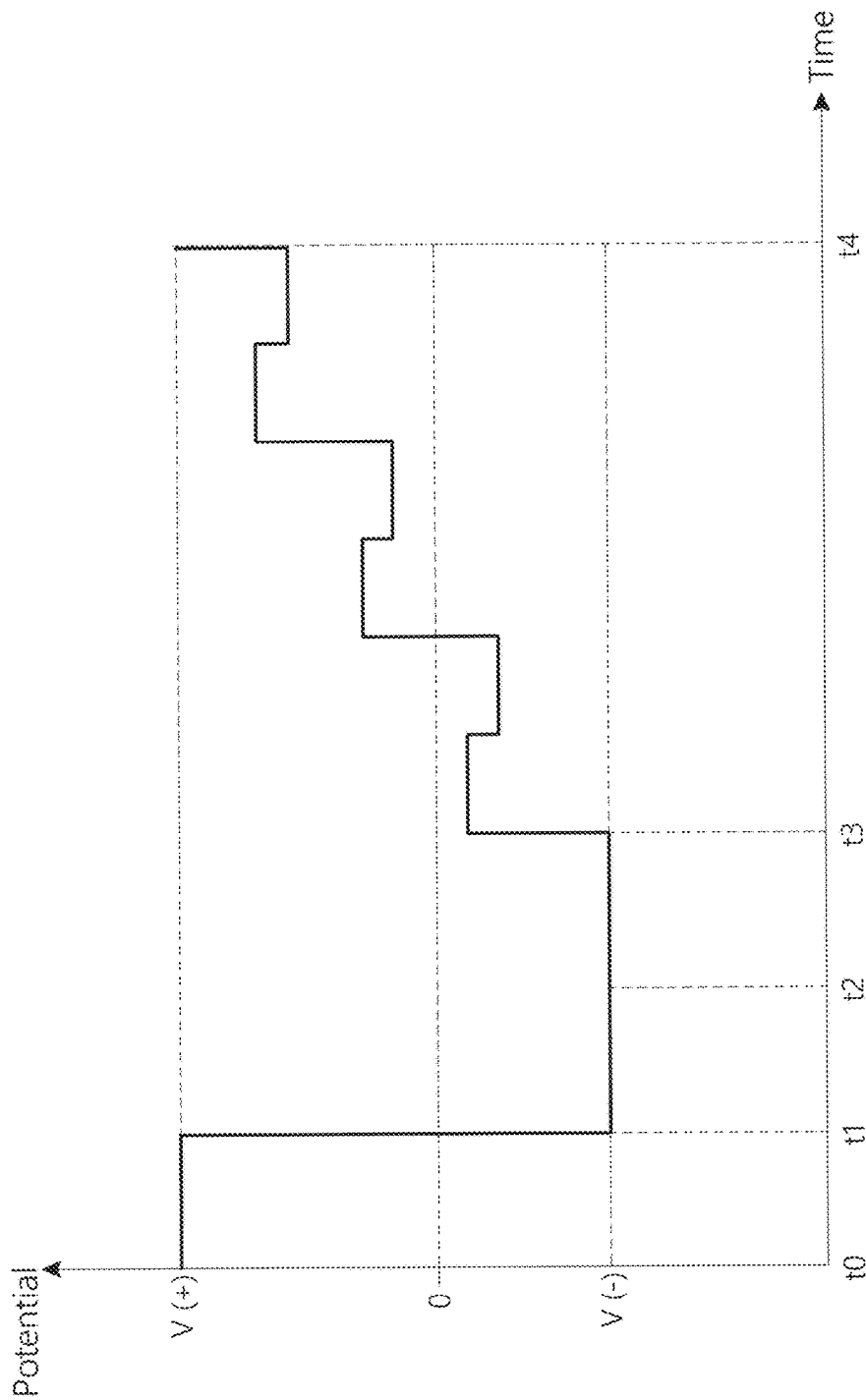
FIG. 9 is an illustration of an exemplary voltage pattern used during an anodic stripping voltammetry test.

Referring to FIG. 9, at time t0, the potential of the fluid in the test chamber 226 can be raised to a predetermined level above the oxidation point of the contaminants of interest. The predetermined potential can be reach by application of a positive voltage via the third electrode (e.g., the counter electrode) 244c to the first electrode (e.g., the working electrode) 244a at a known positive voltage V (+) (e.g., 1 volt, 0.8 volts, 2 volts, or some other appropriate positive voltage). The third electrode 244c can be, for example, a solid or plated aluminum, titanium, silver, gold, or other wire. The first electrode 244a can be a copper wire plated with gold. In some embodiments, the first electrode 244a is constructed from a solid or plated Bi, Al, Ga, In, Sn, Sb, Ir and Ir-oxide, Graphene/Graphite, and/or other materials or combinations of materials such as BiSn, BiSb, InSb, and other alloys. At the initial, raised potential illustrated in FIG. 9, the first electrode 244a is effectively cleaned of analytes and other contaminants having oxidation points lower than the raised potential. Agitation of the fluid in the test chamber 226 distributes the analytes/contaminants throughout the test chamber 226.

At time t1 (e.g., approximately 0.5-1.5 minutes after t0), a negative voltage V (−) is applied via the third electrode 244c to test fluid and first electrode 244a. This lowering of the potential in the test fluid causes the contaminants to undergo an oxidation/reduction reaction at the first electrode 244a and form an amalgam with the gold or other material comprising the first electrode 244a. At a time t2 after the time t1, the agitator is shut off. In some embodiments, the time between t1 and t2 is between 0.5 and 10 minutes (e.g., 500 seconds). At a later time t3, the voltage from the third electrode is swept from the negative voltage V (−) back to the positive voltage V (+). In some embodiments, the time between t2 and t3 is between 0.5 and 10 minutes (e.g., 500 seconds). This sweeping can be in form of a stepped wave, a linear increase, a square wave superimposed on a linear increase (the illustrated pattern of FIG. 9), or some other form. Sweeping the voltage from the third electrode 244c from the negative voltage to the positive voltage causes the contaminants to disperse electrons in the test fluid as the contaminants are released from the first electrode 244a. The current generated by the release of electrons is measured between the counter and working electrodes. The reference electrode is used to provide a common reference point against which the electrochemical reactions are compared.

Figure 10:
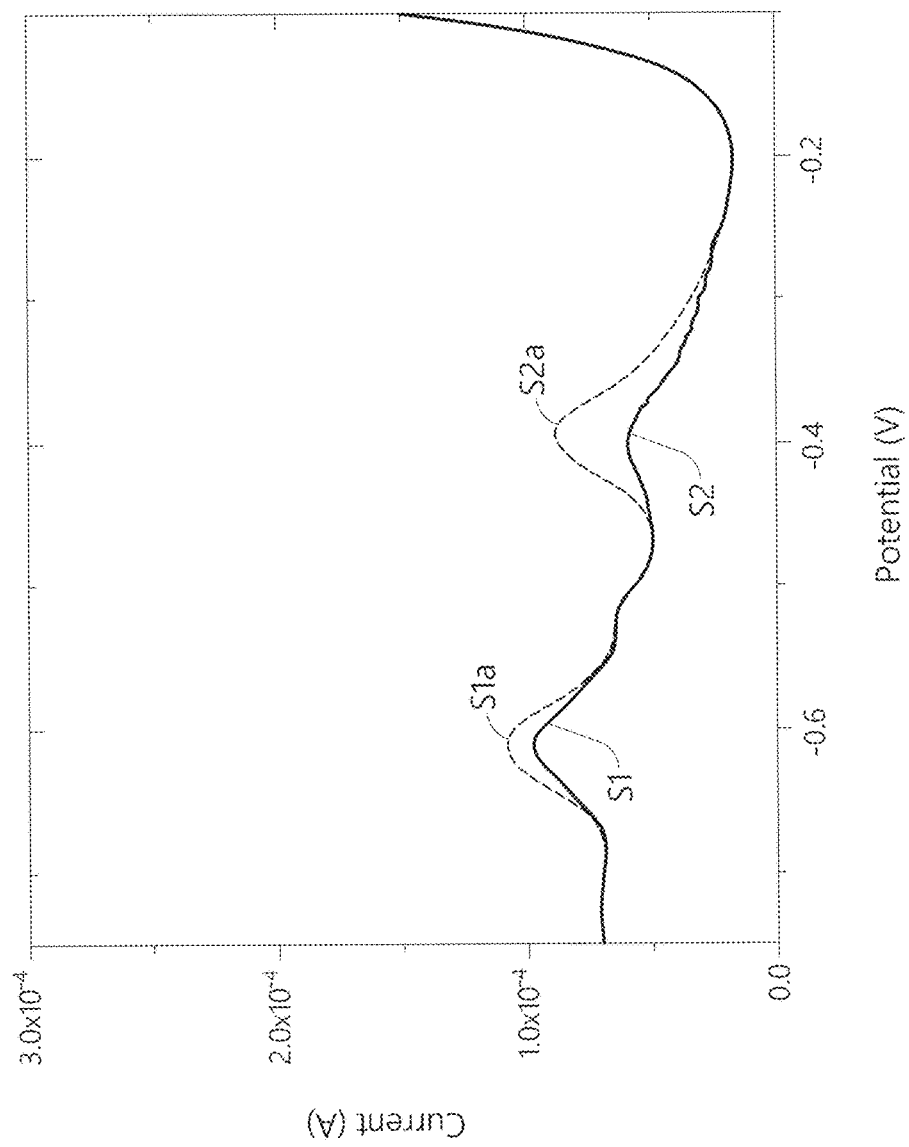
FIG. 10 is an illustration of an exemplary current measurement of an anodic stripping voltammetry test.

The reference electrode can be, for example, a copper wire coated with silver (or one of the wires described earlier with respect to the third electrode). As illustrated in FIG. 10, the release of electrons by the contaminants is measured as spikes S1, S2 at known potentials for the respective contaminants. The magnitude of the spikes corresponds to the amount of contaminant in the test fluid.

After the voltage sweep is complete, the fluid transfer system 227 can be used to move a known amount of fluid from one or more of the chambers 226b, 226c to the test chamber 226. These fluids typically include a known, high concentration of contaminants of interest. The pipette 272 or other fluid collection device can be rinsed in the secondary chamber 226d when desired or needed. The above-described steps are then repeated and a new current readout showing spikes S1a, S2a, having higher peaks than the current spikes realized in the first testing process. The precise amount of contaminant in the test fluid can then be calculated by comparing the peak magnitude increases to the known quantities of contaminant added between the tests. This process can be repeated several times (e.g., 2, 3, 4, 5, 6, 7 or more times), adding a known amount of contaminant between each process. The repetition of measurements with increased known amounts of contaminants can allow the fluid testing system 100 to self-calibrate without the need to compare the test results to standard tables. This can provide faster and more accurate assessments of the levels of contaminants in a given fluid system, in a diverse set of conditions and sample types. The amount of concentrated contaminant added to the test fluid can be modified based on the anticipated level of contamination in the fluid. For example, if high levels of lead are anticipated or measured in an initial sample, then higher levels of known quantities of lead can be added to the test fluid between test cycles to allow for more sensitive detection of lead and vice-versa for scenarios in which the fluid having a known quantity of lead has a lower concentration of lead than the tested fluid.

In between testing cycles, new (e.g., unused) lengths of the electrodes 244a, 244b, 244c can be introduced to the test chamber 226. The testing module 232 can be configured to supply sufficient lengths of electrode wires to allow for periodic testing of the fluid lines for at least 2 months, at least 6 months, at least 1 year, and/or at least 2 years. Using the spool system or other wire feeding mechanism as described above reduces or eliminates the need to provide additional storage for used electrodes or to provide a cleaning mechanism to clean the electrodes. Thus, the overall complexity, costs, and/or size of the system 200 can be reduced. In some applications, it may be desirable to test the fluid of interest for many different contaminants/pollutants. In some such cases, the modular aspect of the test modules 232 can facilitate quick and easy customization of the fluid testing system 200 to test for contaminants and pollutants of interest. Specifically, the easy removal and exchange of the modules 232 can allow for replacement of a first module having a first set of known solutions with a second module having a second set of known solutions. In some cases, the types of one or more electrodes and/or the type of electrolyte used in the first module can be different from the electrode(s) and/or electrolyte of the second module. As described above, different testing modules 132 can be exchanged which include different structures (e.g., structures for measuring pH, temperature, turbidity, etc.). In some case, fluid parameter other than contaminant level can be measured using a testing module 232 having a different, similar, or identical construction to that of testing module 232 described above for use in ASV testing. For example, the three electrodes 244a, 244b, 244c can be used to measure conductivity of the test fluid. More specifically, a known voltage can be applied across two of the electrodes. The current flowing across the two electrodes can be measured and converted to a voltage measurement to evaluate conductivity. In some applications, salinity of the test fluid can be tested. For example, the measured conductivity can be used as an indicator of the total amount of dissolved salts within the test fluid. The salinity/conductivity/turbidity test may be performed in a test chamber separate from the test chamber 126 in which the ASV testing is performed.

The testing modules 232 and/or the packaging within which they are delivered can clearly identify the compositions of the known solutions in the fluid chambers 242. The testing modules 232 can include unique identifiers (e.g., QR codes, bar codes, RF tags, alphanumerical codes, etc.) that can be entered/scanned by an installer to identify the particular testing module 232 and respective fluids/electrodes associated with that testing module. This information can be used to facilitate accurate and precise modification of automatic and/or remote control protocols associated with the control of the fluid testing system 200.

Figure 11:
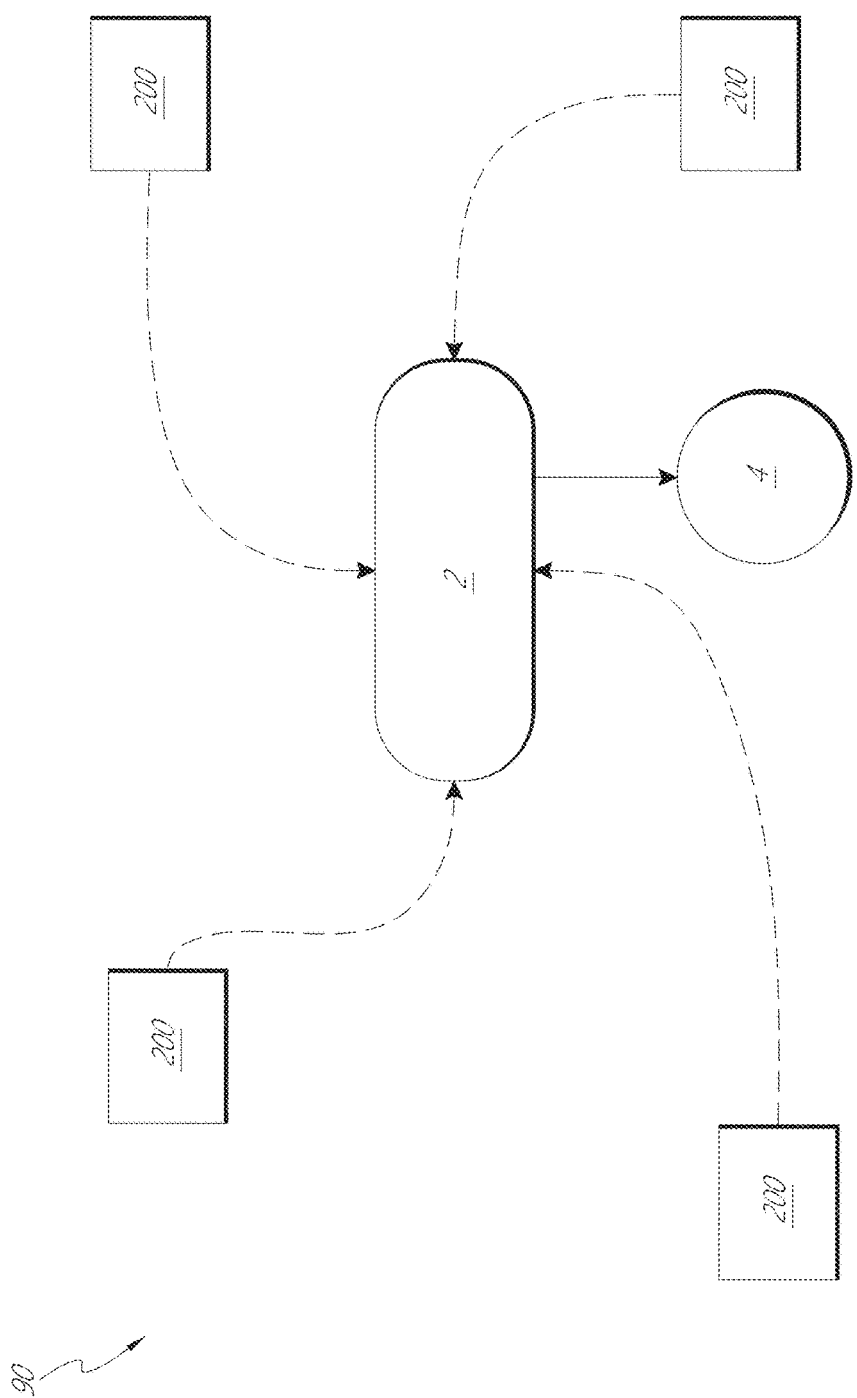
FIG. 11 is a schematic illustration of a fluid testing system.

As illustrated in FIG. 11, a plurality of fluid testing systems 200 can be connected to a cloud network 4 or other network of distributed servers to form a monitoring network 90. For example, each of the fluid testing systems 200 can include a signal generator configured to generate and send signals (e.g., wireless signals) to the cloud 4. This can be accomplished via a Wi-Fi, Bluetooth®, RF transmission, LoRaWAN, Radio/cellular, GSM, or other wireless signal. In some embodiments, two or more of the fluid testing systems 200 can communicate with each other, either wirelessly or via a wired connection. The fluid testing systems 200 and/or network hub(s) 2 can form a mesh network in which communications are sent between the fluid testing systems 200 and network hub(s) 2.

Preferably, the one or more network hubs 2 communicate the signals from the fluid testing systems 200 to the cloud network 4. In some embodiments, all data processing is performed on the cloud network 4 (e.g., the network of distributed servers), without processing on the hub(s) 2 or at the individual fluid testing systems 200. This arrangement can be advantageous for a number of reasons. For example, the design and structure of the fluid testing systems 200 can be simplified due to the lack of a need for data processing. This simplification can reduce the size and/or power consumption of the fluid testing systems 200. In some cases, retaining all data processing on the cloud network 4 can reduce the risk of security compromise if a thief or other bad actor were to obtain an individual fluid testing system 200 or network hub 2.

The communication between the network hub(s) 2, cloud 4, and individual fluid testing systems 200 can be bi-directional. For example, as explained above, the individual fluid testing systems 200 can relay information to the network hub(s) 2 which can, in turn, relay information to the cloud network 4. The system can be configured such that the cloud 4 and/or hub 2 can relay information back to the fluid testing systems 200 to tune, calibrate, or otherwise affect a change in operation of the fluid testing systems 200. Remotely controlling the software on the fluid testing system 200 can facilitate generations of new and/or different data for analyzing large and small-scale water quality characteristics of a given application. Utilizing such functionality with or without mesh network functionality can create a scalable network architecture.

Figure 12:
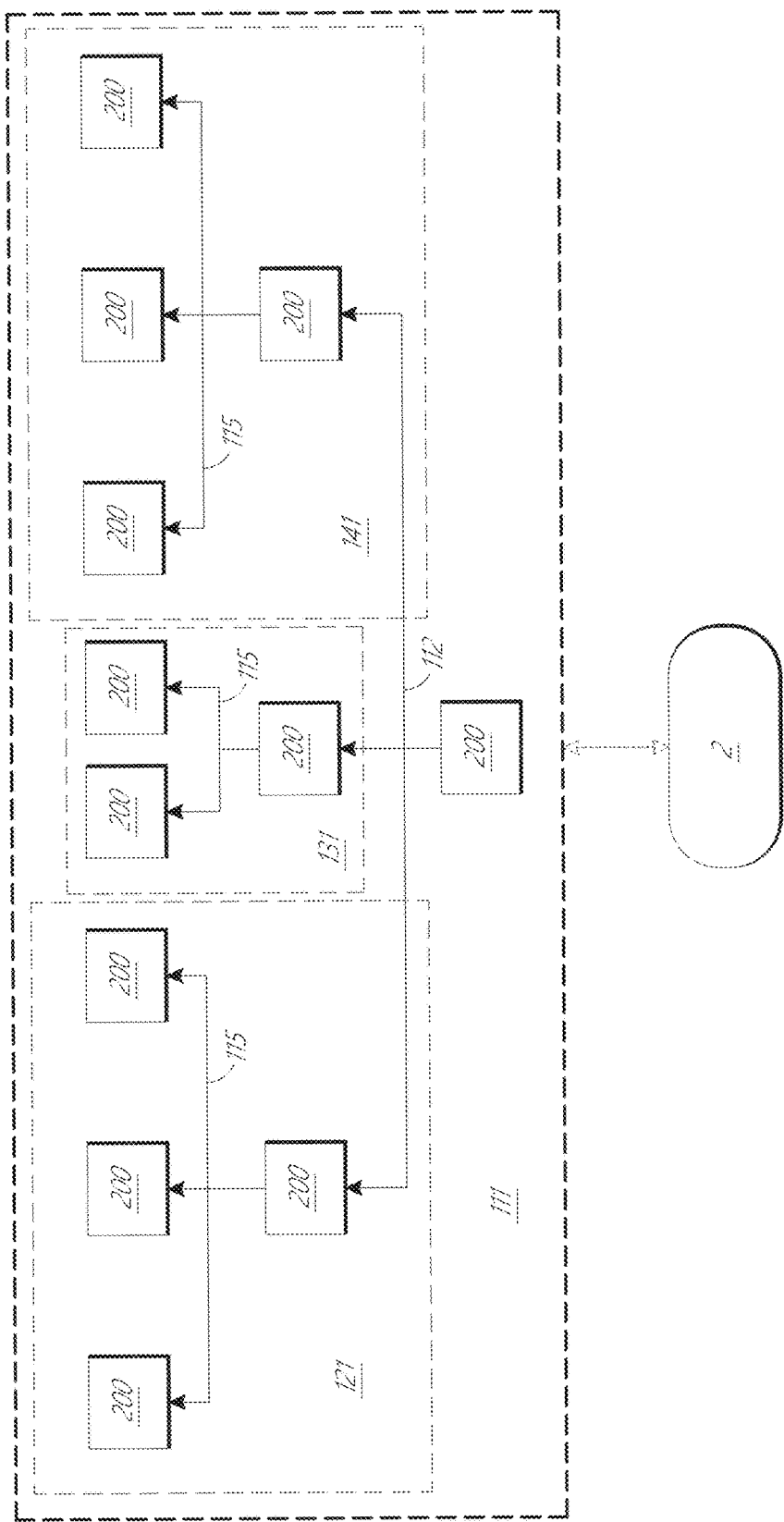
FIG. 12 is a schematic illustration of a fluid testing system as installed in a water flow network.

As illustrated in FIG. 12, the fluid testing systems 200 can be used in a water network 111 comprising a plurality of pipes 112, 115. For example, the fluid testing systems 200 can be positioned in a plurality of generations of piping. As illustrated, at least one fluid testing system 200 can be positioned in line with both first-generation pipes 112 (e.g., pipes connected to a water hub or water source) and second generations pipes 115 (e.g., pipes downstream of the fluid testing systems 200 connected to the first generations pipes 112). The fluid testing systems 200 can be provided with unique identifiers (e.g., QR codes, bar codes, RF tags, alphanumerical codes, etc.) that can be entered/scanned by an installer to identify the particular fluid testing system 200 with a particular position in the water network 111.

The fluid testing systems 200 can provide water/fluid quality information in an on-demand basis. The ability to monitor water characteristics in specified regions of the water network 111 can enable precise and accurate identification of leaks, blockages, clogged/expired filters, mechanical failure, and/or other problems in the water network. For example, the overall arrangement of the water fluid testing systems 200 with respect to the pipes 112, 115 is known by the service provider who, in turn, can group the water fluid testing systems 200 in any number of groupings 121, 131, 141. If an abnormal level of contaminants were detected in a first group 121 of systems, but contaminant levels appeared as expected in a second group of systems 131, the technician or other service provider could quickly identify the portion of pipe or the particular fluid testing system 200 having the problem or deficiency. In other words, the unique identification of the water fluid testing systems 200 with respect to their location in the water network 111 can facilitate expedient and accurate identification of defective pipes and systems based upon the information contemporaneously gathered by the fluid testing systems 200 through the system 111 and groupings 121, 131, 141. Exemplary water networks 111 could include public utilities, mining locations, fracking locations, groundwater monitoring systems, agricultural arrays, farming and rural water distribution systems, beverage manufacturing facilities, food and beverage facilities (e.g., dairy facilities, drinking water facilities, bottling facilities), commercial businesses, environmental locations (e.g., parks, reservoirs, rivers, lakes, rivulets, etc.), or any other water grid, network, or storage system.

The information and data gathered from each fluid testing system 200 can be stored in the cloud network 4 or elsewhere. The stored information can be correlated to a given fluid testing system 200, given location, given user, given appliance, and/or to some other unique identifier. The storage of such correlated data can facilitate faster and more accurate analysis of the live data provided by the fluid testing systems 200. For example, live monitor data indicative of leaks or blockages can be correlated to historic monitor data and/or data from fluid testing systems 200 in other locations to further confirm the accuracy of the live monitor data. The data correlation also helps proactively identify health risks in regions associated with the monitoring for public safety, water safety, and/or food safety.

Figure 13:
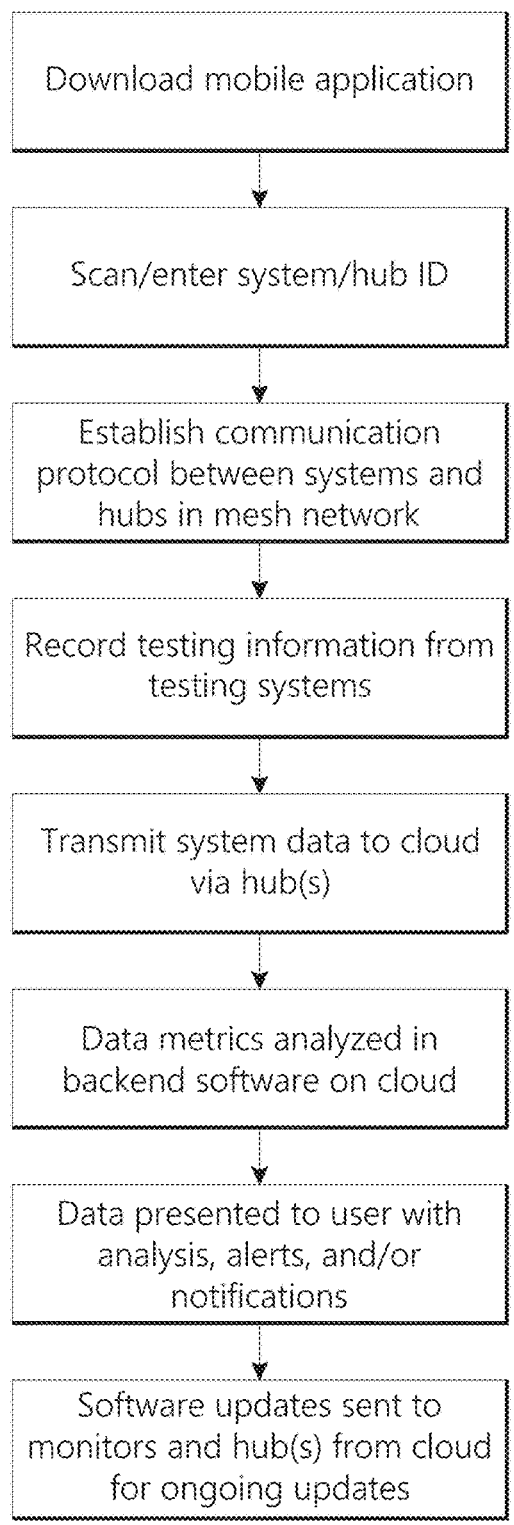
FIG. 13 is a flow chart of an embodiment of an operating process of a fluid testing system.

FIG. 13 illustrates a process of using the network 90. To begin, a user or installer of the systems can download a mobile application configured to facilitate installation of the fluid testing systems 200 and/or hub(s) 2. In some cases, the installer can use a hardware device pre-programmed with installation software. The installer can then install the fluid testing systems 200 and hubs 2 in the desired locations for monitoring. Prior to or after installation of the fluid testing systems 200 and hubs 2, the installer can scan or otherwise enter unique identification information from the fluid testing systems 200 and hubs 2. Such unique identification information can include a barcode, QR code, alphanumeric code, color coding, an RF ID, or some other unique identifier. The fluid testing systems 200 and hubs 2 can be configured automatically establish communication protocols between each other and the network of distributed servers 4. In some applications, the installer or user establishes such protocols. The communication protocols can establish a mesh network of fluid testing systems 200 and/or hub(s) 2 with a complete cloud based management for collection, presentation, and analysis of data and to handle failure scenarios and recovery with scale.

The network 90 can be configured to monitor the test data from the fluid testing systems 200 in real time and to transmit the test data to the cloud 4 via the one or more hub(s) 2. The test data (e.g., currents, voltages, etc.) can be analyzed on the cloud 4. The data and/or analysis can be presented to the user. Such presentation can include alerts, warnings, requests for maintenance, and/or other reports. The cloud 4 can push software updates and/or other communications back to the fluid testing systems 200 and hubs 2 to facilitate efficient and reliable operation of the network 90.

For expository purposes, the term "horizontal" as used herein is defined as a plane parallel to the plane or surface of the floor of the area in which the system being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated," and other such relational terms should be construed, unless otherwise noted, to include removable, moveable, fixed, adjustable, and/or releasable connections or attachments. The connections/attachments can include direct connections and/or connections having intermediate structure between the two components discussed.

The terms "approximately", "about", "generally" and "substantially" as used herein represent an amount close to the stated amount that still performs a desired function or achieves a desired result. For example, the terms "approximately", "about", "generally," and "substantially" may refer to an amount that is within less than 10% of the stated amount.

While the preferred embodiments of the present inventions have been described above, it should be understood that they have been presented by way of example only, and not of limitation. It will be apparent to persons skilled in the relevant art that various changes in form and detail can be made therein without departing from the spirit and scope of the inventions. Thus, the present inventions should not be limited by the above-described exemplary embodiments, but should be defined only in accordance with the following claims and their equivalents. Furthermore, while certain advantages of the inventions have been described herein, it is to be understood that not necessarily all such advantages may be achieved in accordance with any particular embodiment of the inventions. Thus, for example, those skilled in the art will recognize that the inventions may be embodied or carried out in a manner that achieves or optimizes one advantage or group of advantages as taught herein without necessarily achieving other advantages as may be taught or suggested herein.

What is claimed is:

1. A fluid testing system that performs a plurality of test cycles on fluid comprising:
    a housing having inlet that attaches to a fluid line and an outlet that attaches to the fluid line;
    at least one testing chamber in the housing that receive fluid from the inlet of the housing;
    a fluid movement assembly that selectively directs fluid from the inlet into the at least one testing chamber;
    a wire feed system that provides first and second electrodes to the at least one testing chamber, wherein the wire feed system includes a length of first and second electrodes wires and wherein the wire feed system provides a new portion of the length of the first and second electrodes for each test cycle;
    a reference sample supply system that supplies reference samples to the at least one testing chamber;
    a control system that controls the fluid movement assembly, the wire feed assembly and the reference sample supply system such that for each test cycle, the at least one testing chamber is filled with fluid and a new portion of the first and second electrodes are positioned into the at least one testing chamber, and wherein the control system applies an electric signal the electrodes and samples the results so as to determine the presence of selected contaminants in the fluid in the at least one testing chamber; and
    a third electrode, wherein the first electrode is a working electrode, the second electrode is a counter electrode, and the third electrode is a reference electrode;
    wherein the control system is configured to apply a positive voltage from the counter electrode to the working electrode, then to apply a negative voltage from the counter electrode to the working electrode, then to transition from the negative voltage back to the positive voltage, wherein the control system measures current and voltage relative to the reference electrode to determine an amount of at least one selected contaminant in the fluid in the testing chamber.

2. The system of claim 1, wherein the control system for each testing cycle induces the delivery of the fluid to be tested, performs a first measurement by application of an electric signal to the first electrode, determines a first measurement indicative of the presence of a selected contaminant in at least one testing chamber by evaluating a signal received on a second electrode in response to the electric signal, then induces the supply of a known quantity of the selected contaminant to the at least one testing chamber and performs a second measurement by application of the electric signal to the first electrode and determines a second measurement indicative of the presence of the selected contaminant on the signal received on the second electrode in the at least one testing chamber.

3. The system of claim 2, wherein the control system determines the quantity of contaminant present in the at least one testing chamber by determining the difference between the first and second measurements.

4. The system of claim 1, wherein the wire feed system comprises at least one supply spool positioned within the housing and around which an unused quantity of at least one of the first and second electrode wires is wrapped, the wire feed system including an electrode movement apparatus configured to move an unused portion of each of the first and second electrodes into the at least one testing chamber after each test cycle is completed.

5. The system of claim 4, wherein the electrode movement apparatus comprises a collecting spool around which a portion of at least one of the first and second electrodes is wrapped.

6. The system of claim 5, comprising a motor configured to rotate the collecting spool, wherein the motor is controlled by the control system.

7. The system of claim 4, wherein the wire feed system is positioned in an electrode module configured to be removable from the housing.

8. The system of claim 7, wherein the electrode module includes a volume of fluid having a known concentration of a selected contaminant, and wherein the electrode module is configured to output the volume of fluid into a constituent chamber in the housing separate from the electrode module when the electrode module is installed in the housing.

9. A fluid testing system that performs a plurality of test cycles on a fluid comprising:
    a housing having an inlet that attaches to a fluid line and an outlet that attaches to the fluid line;

at least one testing chamber in the housing that receives fluid from the inlet of the housing;
a first electrode;
a second electrode;
a fluid supply system that supplies fluid samples to the at least one testing chamber, each fluid sample including a known concentration of at least one contaminant;
a control system that is configured to control the fluid sample supply system such that for each test cycle, the at least one testing chamber is filled with fluid, wherein the control system is configured to apply an electric signal to the first electrode and samples the results so as to determine the presence of selected contaminants in the fluid in the at least one testing chamber, wherein the control system is configured to induce the addition of a known amount of a selected contaminant to the fluid received from the inlet of the housing in the at least one testing chamber and reapplies the electric signal and re-samples the results, and wherein the results of the re-sampling are compared to the results of the sampling to determine the amount of the selected contaminant in the fluid; and
a wire feed system that provides the first and second electrodes to the at least one testing chamber, wherein the wire feed system includes a length of first and second electrodes wires and wherein the wire feed system provides a new portion of the length of the first and second electrodes for each test cycle, and wherein the control system is configured to control operation of the wire feed system.

10. The system of claim 9, comprising a wired or wireless signal generator in electrical communication with the control system, wherein the wireless signal generator generates wireless signals including the results of the sampling on the second electrode.

11. The system of claim 9, comprising a unique identifier, wherein the unique identifier is used to correlate the results sampled by the control system with the physical location of the system.

12. The system of claim 9, wherein the control system is configured to operate via remote control and/or by preset automated control.

13. A method of measuring levels of one or more contaminants in a fluid, the method comprising:
passing a test volume of fluid through an inlet of a housing into a test chamber within the housing;
adding a predetermined volume of acid to the test chamber;
introducing a first test length of a first electrode wire into the test volume;
introducing a first test length of a second electrode wire into the test volume;
introducing a first test length of third electrode wire into the test volume;
applying a positive voltage from the third electrode to the first electrode for a first period of time;
applying a negative voltage from the third electrode to the first electrode for a second period of time;
transitioning from the negative voltage back to the positive voltage over a third period of time;
measuring current and voltage in the fluid in the test chamber relative to the second electrode;
after the measuring step, adding a known quantity of fluid having a known concentration of a selected contaminant to the test chamber and then repeating the applying, transitioning, and measuring steps;
determining an amount of the selected contaminant in the test volume of fluid by comparing the measured currents and voltages from before and after the adding of the known quantity of fluid having a known concentration of the selected contaminant.

14. The method of claim 13, comprising:
moving the first test length of first electrode wire out from the test volume and moving a second test length of first electrode wire into the test volume, the second length connected to the first length;
moving the first test length of second electrode wire out from the test volume and moving a second test length of second electrode wire into the test volume, the second length connected to the first length; and
moving the first test length of third electrode wire out from the test volume and moving a second test length of third electrode wire into the test volume, the second length connected to the first length;
wherein the moving steps are performed by an electrode transition mechanism configured to selectively move the first, second, and third electrodes through the test volume.

15. The method of claim 14, wherein the determining step is performed before the moving steps.

16. The method of claim 15, wherein the step of transitioning from the negative voltage back to the positive voltage is performed using a square wave or differential wave superimposed on a linear voltage increase or stepped voltage increase.

17. The method of claim 13, wherein the first electrode is a working electrode, the second electrode is a reference electrode, and the third electrode is a counter electrode.

* * * * *